United States Patent
Scott et al.

(10) Patent No.: US 6,468,212 B1
(45) Date of Patent: *Oct. 22, 2002

(54) USER CONTROL INTERFACE FOR AN ULTRASOUND PROCESSOR

(75) Inventors: Walter Guy Scott, North Palm Beach; Albert Vera, Coral Gables, both of FL (US)

(73) Assignee: Adalberto Vara, Coral Gables, FL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/148,093

(22) Filed: Sep. 3, 1998

Related U.S. Application Data

(63) Continuation of application No. 08/835,463, filed on Apr. 19, 1997, now abandoned.

(51) Int. Cl.$^7$ .................................................. A61B 8/00

(52) U.S. Cl. ....................................... 600/437; 600/440

(58) Field of Search ....................... 705/3; 73/625–633; 378/98; 345/348, 349; 600/437, 440

(56) References Cited

U.S. PATENT DOCUMENTS 5,161,535 A * 11/1992 Short et al.
5,367,316 A * 11/1994 Ikezaki

FOREIGN PATENT DOCUMENTS

| EP | 0533 976 A1 | * | 3/1991 |
| EP | 0744159 A1 | * | 11/1996 |
| EP | 0833266 A2 | * | 4/1998 |

OTHER PUBLICATIONS

Brinkley et al., Ultrasonic Three–Dimensional Imaging And Volumn From A Series Of Arbitrary Sector Scans, Center fo Bioengineering University of Washington, Seattle, USA, Ultrasound in Med. & Biol. vol. 4, pp 317–327, Pergaman Press LTD, 1978.*

* cited by examiner

Primary Examiner—Frantzy Poinvil
(74) Attorney, Agent, or Firm—Thomas R. Vigil

(57) ABSTRACT

The virtual control user interface for an ultrasound processor includes a software driven display obtained from a memory unit in the ultrasound processor and displayed on a display monitor (part of the ultrasound processor) under control of a processor unit (which is also part of the ultrasound processor). The software driven display reveals images representative of hardware control configurations for other ultrasound processors. The images provided by the software driven display and displayed by on the display include: a plurality of gain control tactile user interfaces, a plurality of ultrasound image enhancement control tactile user interfaces and, at least one focused control tactile user interface. The software driven display has multiple menu levels for the display of the gain control images, the ultrasound images enhancement control images and the focused control image. The software driven display is also further configured to reveal images of more than one ultrasound processor. In a further embodiment, the virtual control user interface is used in conjunction with a touch sensitive user input screen and the virtual control user interface includes a touch screen input command converter responsive to a user's touch on the touch sensitive display monitor to convert the tactile input into a software command corresponding to the image proximally displayed on touch sensitive display monitor. Other features include the ability to recall previously scanned ultrasound images, to annotate recently acquired ultrasound images and provide a checklist for medical protocol involved in the ultrasound medical techniques. The medical protocol is loaded as pull down or pop up menu available to the user.

2 Claims, 19 Drawing Sheets

FIG. 3A

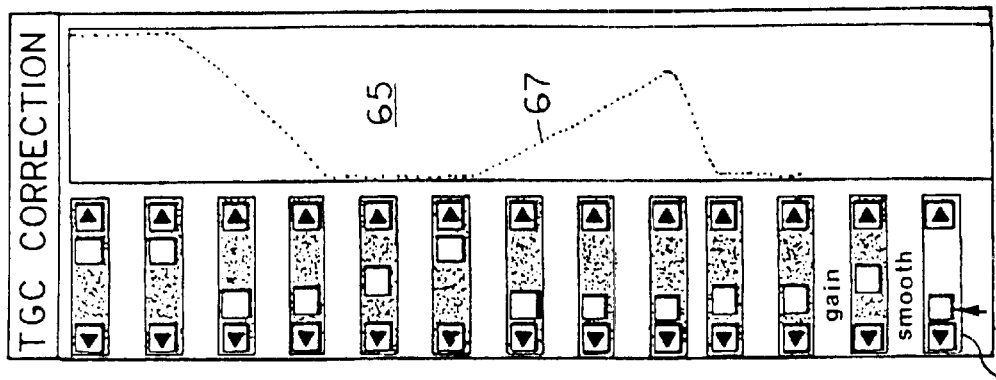
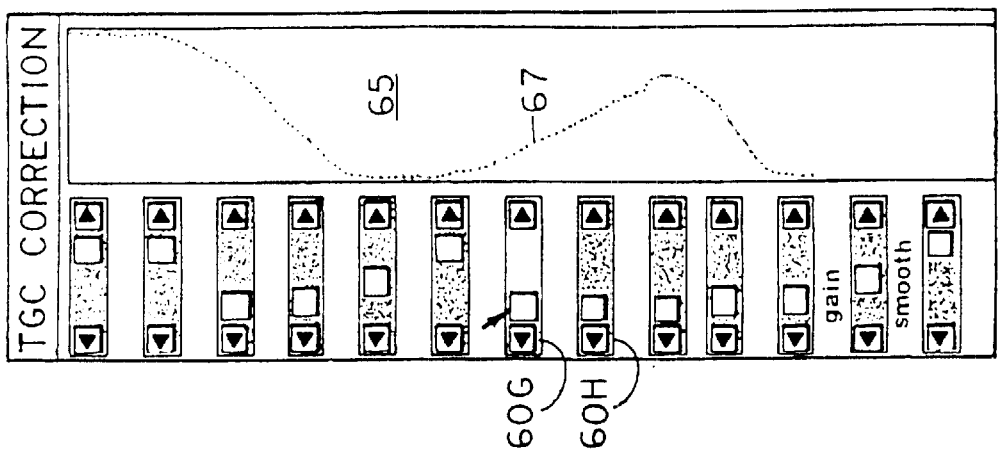
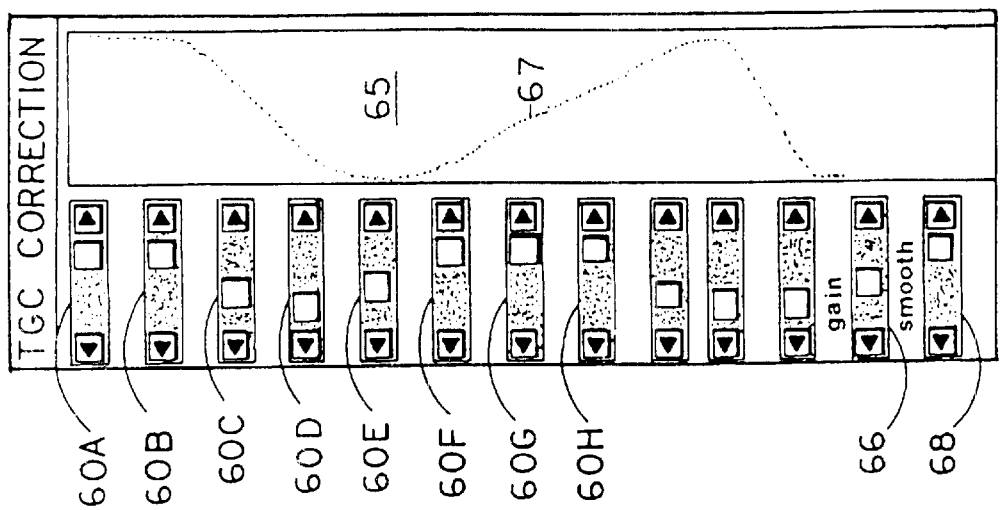
FIG. 4A
FIG. 4B
FIG. 4C

FIG. 11

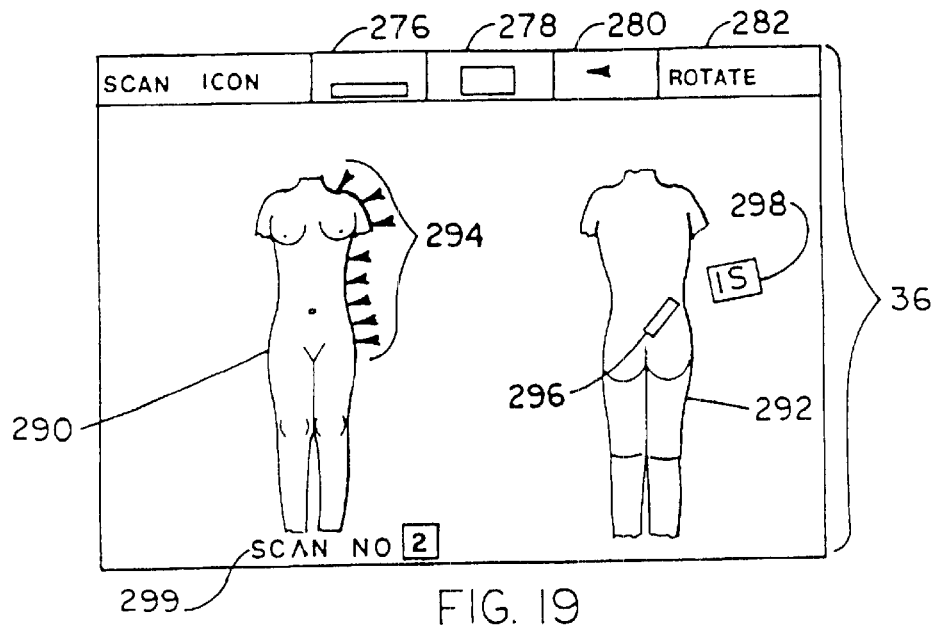
FIG. 19
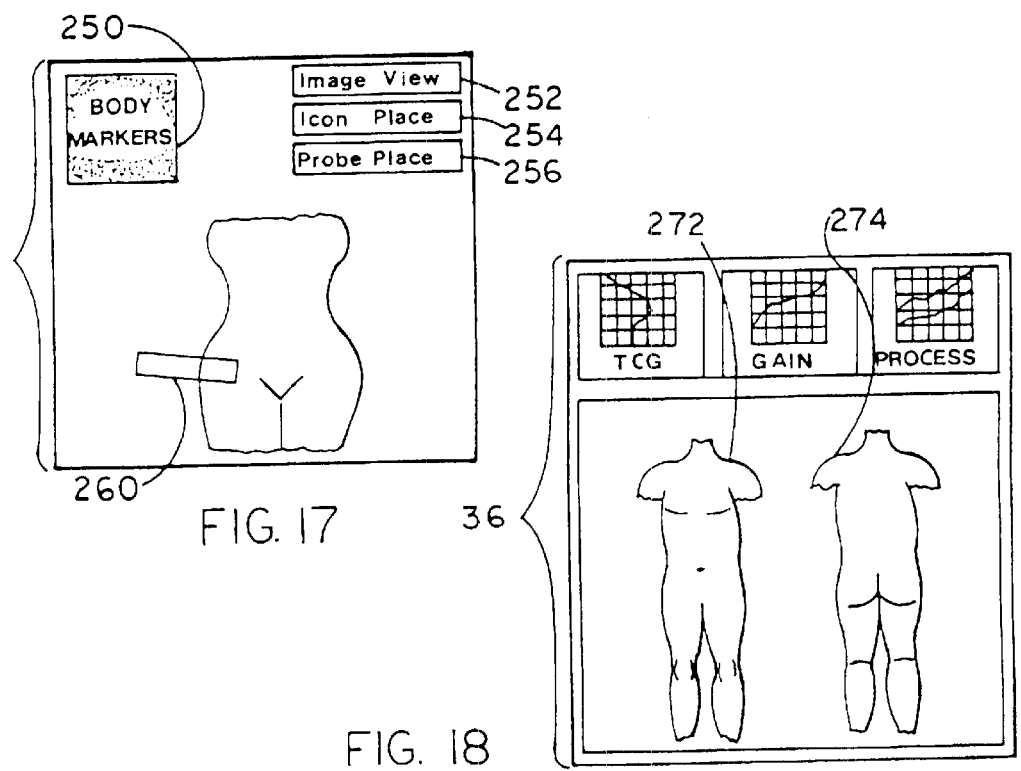
FIG. 17
FIG. 18

USER CONTROL INTERFACE FOR AN ULTRASOUND PROCESSOR

This Appnl is a con't of Ser. No. 08/835,463 filed Apr. 8, 1997 ABN.

BACKGROUND OF THE INVENTION

The present invention relates to a virtual control user interface for an ultrasound processor and a method there for which mimics the hardware configuration for other ultrasonic processors.

Ultrasound is utilized in many non-invasive medical procedures in order to detect and diagnosis a patient's condition. For example, ultrasonic scans are commonly used to detect and monitor the growth, viability and health of fetuses, to detect and assist in the diagnosis of liver, kidney, and other intestinal ailments, among others.

During these procedures, an ultrasound transducer head is placed atop or near the internal organ sought to be scanned. The ultrasonic image (generally resulting from the detection of sonic echoes by the ultrasonic transducer head) is displayed in essentially real time on a display monitor.

A significant number of ultrasound machines utilize user interfaces which are configured as knobs, slide switches, push buttons and other similar type tactile controls. The user must be trained to simultaneously hold the ultrasonic scan head on the body of the patient while adjusting the knobs, push buttons and slide controls on the ultrasound processor while further viewing the display monitor.

A difficulty arises when the physician or medical office wishes to upgrade the ultrasonic scan head or which is to replace or enhance the ultrasound processor unit electronically coupled to and driving the ultrasound scan head. In general, these ultrasound processor units were simply replaced with a larger enhanced model with a higher level of tactile control knobs, slide switches and push buttons. Of course, the number of tactile controls available to the user has a physical limitation in relation to the size of the overall processor unit. Further, the physician or medical office is required to train the use of the machine and this training is unique to a particular hardware and ultrasonic processing technique.

OBJECTS OF THE INVENTION

It is an object of the present invention to provide a computer based virtual control user interface for an ultrasound processor.

It is a further object of the present invention to provide a virtual control user interface which incorporates multiple menu levels for the display of gain control images, ultrasound enhancement control images and focused controlled images.

It is a further object of the present invention to provide a virtual control user interface which can reveal images representative of hardware control configurations for a number of ultrasound processors.

It is an additional object of the present invention to provide a virtual control user interface which incorporates a touch screen display monitor.

It is another object of the present invention to provide a virtual control user interface which can be customized by the user to enhance the operability and effectiveness of the user interface.

It is a further object of the present invention to provide a virtual control user interface which includes a pull down or pop up protocol check list or menu which may be used by the user to insure that the ultrasound techniques recorded by the ultrasound processor comply with a predetermined medical protocol.

It is another object of the present invention to provide an ultrasound processor which is configured with plug-in boards for a processor unit, input/output interface or display monitor, a keyboard, and various input/output interfaces for other peripheral computer equipment.

SUMMARY OF THE INVENTION

The virtual control user interface for an ultrasound processor includes a software driven display obtained from a memory unit in the ultrasound processor and displayed in a display monitor (part of the ultrasound processor) under control of a processor unit (which is also part of the ultrasound processor). The software driven display reveals images representative of hardware control configurations for other ultrasound processors. These ultrasound processors are electronically coupled to an ultrasound scan head via a scan head interface unit. The image provided by the software driven display and displayed by on the display include: a plurality of gain control tactile user interfaces, a plurality of ultrasound image enhancement control tactile user interfaces and, at least one focus control tactile user interface. The software driven display has multiple menu levels for the display of the gain control images, the ultrasound images enhancement control images and the focus control image. The software driven display is also further configured to reveal images of more than one ultrasound processor. In a further embodiment, the virtual control user interface is used in conjunction with a touch sensitive user input screen and the virtual control user interface includes a touch screen input command converter responsive to a user's touch on the touch sensitive display monitor to convert the tactile input into a software command corresponding to the image proximally displayed on touch sensitive display monitor. Other features of the control user interface include the ability to recall previously scanned ultrasound images which are recorded in the memory unit of the ultrasound processor, to annotate recently acquired ultrasound images, preferably in color, such that the ultrasound electronic images and associated annotations can be electronically transferred from the ultrasound processor to other peripheral computer equipment, and a checklist for medical protocol involved in the ultrasound medical techniques. The medical protocol is loaded as pull down or pop up menu available to the user.

BRIEF DESCRIPTION OF THE DRAWINGS

Further objects and advantages of the present invention can be found in the detailed description of the preferred embodiment when taken in conjunction with the accompanying drawings in which:

FIGS. 4A, 4B and 4C diagrammatically illustrate the TGC user interfaces in another embodiment;

FIG. 11 diagrammatically illustrates another embodiment for the caliper or measurement control user interface;

FIGS. 17, 18 and 19 diagrammatically illustrate the body marker or scan region menus and displays in accordance with the principles of the present invention;

DETAILED DESCRIPTION OF THE PREFERRED EMBODIMENT

The present invention relates to virtual control user interface for an ultrasound processor, a method for establishing and using that virtual control user interface, an ultrasound processor having a high degree of inter-connectivity with other computer peripheral equipment, and an ultrasound processor that is configured with plug-in electronic boards generally similar in nature to a personal computer.

Figure 1:
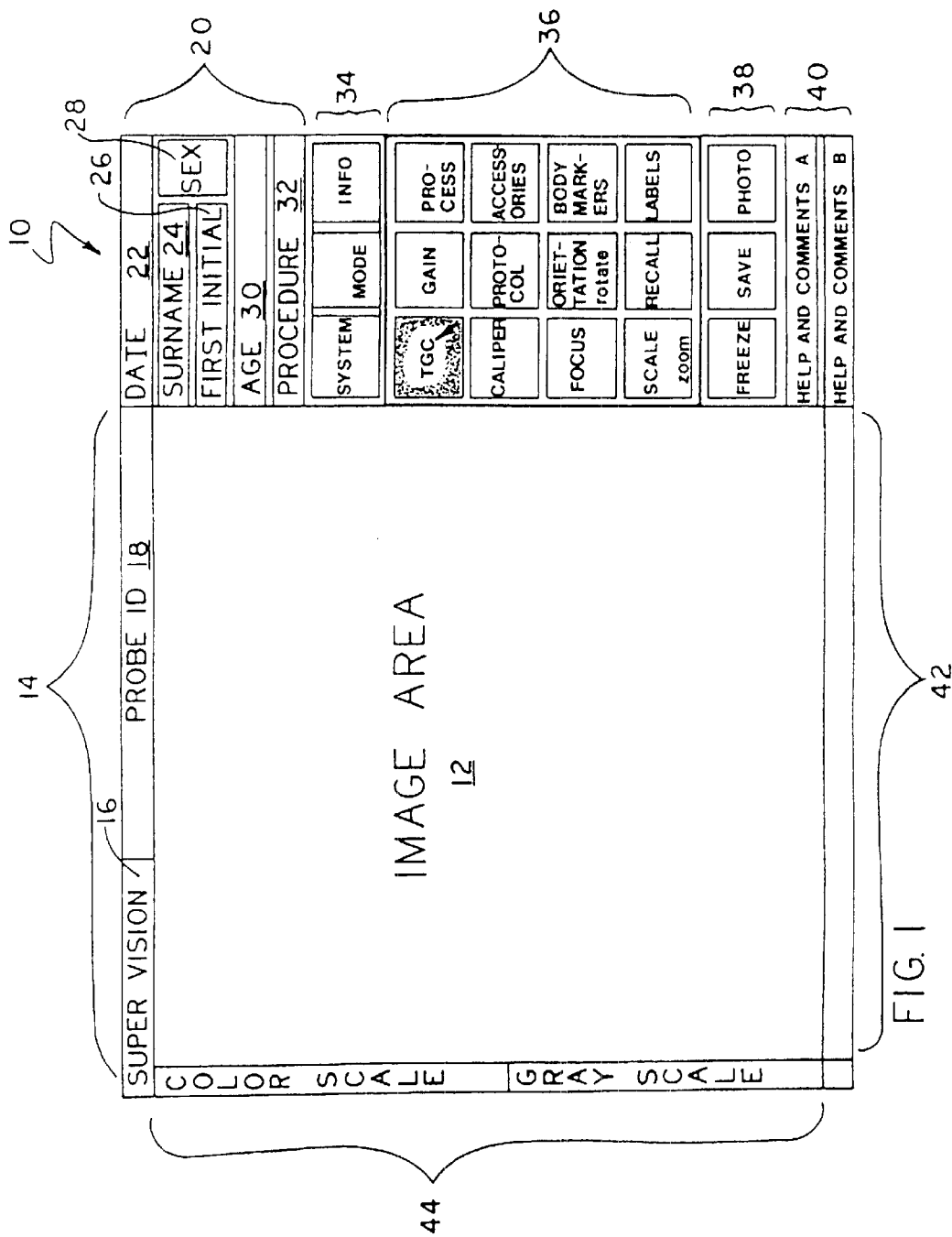
FIG. 1 diagrammatically illustrates one embodiment of the virtual control user interface main screen.

FIG. 1 diagrammatically illustrates one embodiment of the computer based virtual control user interface and particularly the main or primary menu display screen revealing the first electronic representation of a hardware control panel for another ultrasound processor. Main menu display screen 10 includes an ultrasound scan image area 12 (occupying approximately 60–80% of the display monitor) (see FIG. 25 and the accompanying explanatory text for a description of the apparatus). The main menu display screen includes nine major regions one of which is the ultrasound scan image area 12. The sound major region 14 is configured at the upper portions of the screen and includes a program identification area 16 (identify the program as SUPERVISION) and a probe identification or ultrasound scan head identification region 18. It should be noted that the present invention may be used in conjunction with several different types of ultrasound scan heads and therefore it may be important to display the type of scan head currently being utilized by the operator on a continuous basis during the ultrasound procedure. The upper menu region with software program area 16 and probe Id area 18 is generally displayed continuously.

The third screen region 20 includes a date display area 22, a surname or last name display area 24 (showing the last name of the patient currently being scanned by the user or operator of the ultrasound processor), the first initial of the person being scanned 26, the sex of the person being scanned at area 28, the age of the person being scanned at area 30, and a display region 32 showing the particular ultrasonic scanning procedure being carried out by the user on that patient. In general, the information in display screen region 20 is maintained throughout the ultrasound scan.

Display screen regions 34, 36 and 38, respectively, reveal system or equipment configurations (area 34), a dynamic control menu screen region 36, and a critical function menu or screen region 38. The dynamic menu control panel 36 is primarily altered to reset sub-menus and for increasing details of user acceptable controls through generation of the virtual control user interface. However, other changes to the image screen area 12 as well as the help and comment in A' and A B in screen region 40 are discussed in detail hereinafter.

The lower menu bar 42 has been left blank in the embodiment illustrated in FIG. 1. This area can be subject to future development and can be used to display prompts for function keys or other items which may assist the user in controlling the processing as well as the operation of the ultrasound scan head.

The last portion of the display screen 10 is the side bar menu display 44 which provides an indication to the user of the color selected on the display monitor as well as the intensity or gray scale of the image.

As discussed later in conjunction with the TGC and the focus control, the user can alter the gray scale or the color of the ultrasound image displayed in image area 12 by moving the cursor to the tab or bar on the color or gray scale screen region (see FIG. 4A showing a bar), actuating the mouse or track ball control and "dragging" the tab, bar or pointer along the scale. This "pointer click and drag" control alters the image in image area 12. Similar image processing techniques are discussed in conjunction with the TGC, the focus and the video image "process" control discussed hereinafter.

Preferably, the screen display region 28 reveals a small image of a man or a woman rather than simply a designation of M for male or F for female.

Figure 24:
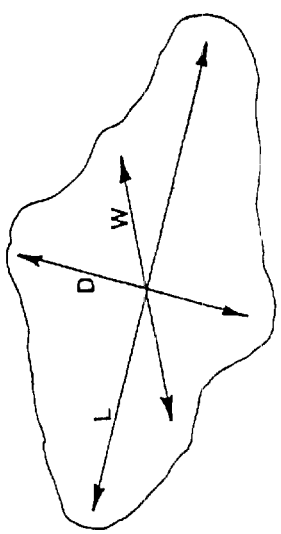
Figure 25:
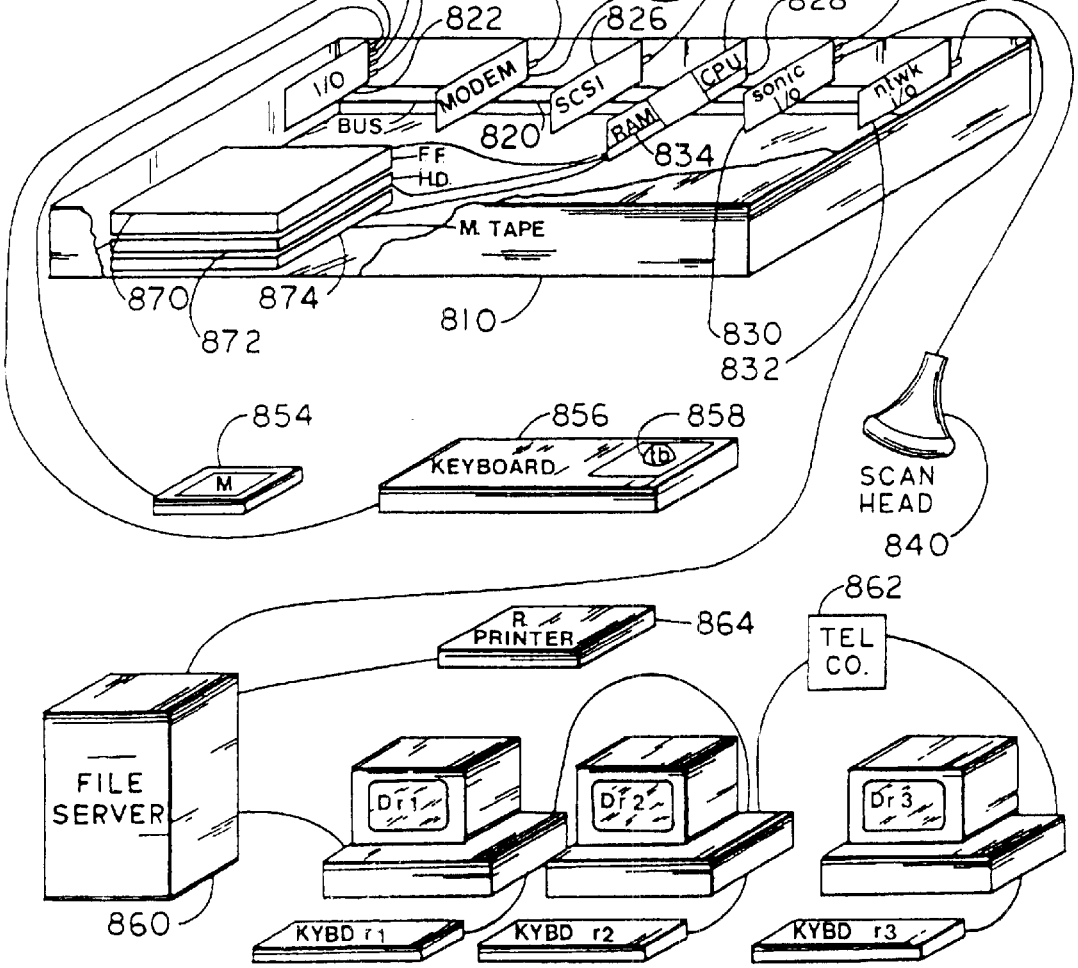

As discussed in detail with respect to FIG. 25, the display menus generally illustrated in FIGS. 1–24 are shown on a display monitor. The display monitor may be a common cathode tube or other display monitor customarily associated with computer equipment or may be a more sophisticated touch screen monitor. As is known by persons of ordinary skill in the art, monitors are available that detect the presence or absence of a user's finger on a certain portion of the screen. This type of display monitor is identified herein as a "touch screen display monitor". The touch screen display monitors are meant to cover devices that are capable of displaying various indicia and images as well as providing an input device for the user to select one or more control functions visually indicated on the display screen.

As discussed later in conjunction with FIG. 25, the user may select one or more elements or menu features from the main menu display screen 10 by use of a cursor directed by a mouse (as shown in FIG. 1) or track ball or by use of the tab key or other key stroke combination.

In any event, when the cursor falls within one of the operable menu blocks, principally display screen areas 34, 36 and 38 the particular element in that menu block lights up or is preliminarily activated such that the user has a visual indication of the precise location of the cursor. It should be noted that the particular menu and sub-menu for that function has not been activated until the user depresses the activation button on the mouse, track ball or strikes the enter or return key on the keyboard. For touch type screens, the user must strike the screen segment immediately proximate the desired function.

In FIG. 1, the cursor has been positioned atop the TGC or time gain control of the ultrasound processor virtual control user interface. The TGC control is lit as shown by the illumination lines. When the cursor arrives at a certain menu block, help and comments area A (display screen area 40) indicates the English language equivalent for that command function. The Comment A Table which is set forth below provides exemplary comments which would appear in the upper portion of the display screen area 40.

| Comment A Table | |
| --- | --- |
| Cursor Position | Comment |
| TGC | Time Gain Control |
| Gain | Power-Gain-Reject |
| Process | Select Correct Process |
| Caliper | Measure Between Points |
| Access | Select Peripheral Accessories |
| Focus | Select Focus Points |
| Body | Id Scan Area on Body |
| Label | Annotate Image |

One important feature of the present invention is the ability of the virtual control user interface to display in the help and comment area 40 a foreign language equivalent for the TGC. Also, another important feature of the present invention enables the user to preset certain elements and textual explanatory material in help and comment area B (display screen area 40) for example, the control user interface could be pre-programmed such that the user would be required to select a particular ultrasonic scan medical protocol for adjusting the TGC or time gain control for the ultrasound scan head. The help and comment area B could automatically remind the user that he or she must select the appropriate medical protocol for adjusting the TGC control on the ultrasonic scan head.

To carry this computer based and computer driven display system one step further, the virtual control user interface could block access to the subsidiary menus (for example, subsidiary menus in FIGS. 3, 4 and 5) until the user actually selects a medical protocol.

Further software blocks could be added to the virtual control user interface which would require the user to input the name, age and sex of the patient and particularly identify the patient number or other relevant information before conducting an ultrasonic scan.

FIGS. 2, 3, 4A, 4B and 4C diagrammatically illustrate two embodiments of the subsidiary menu or secondary menu level below the time gain control TGC user interface.

Figure 2:
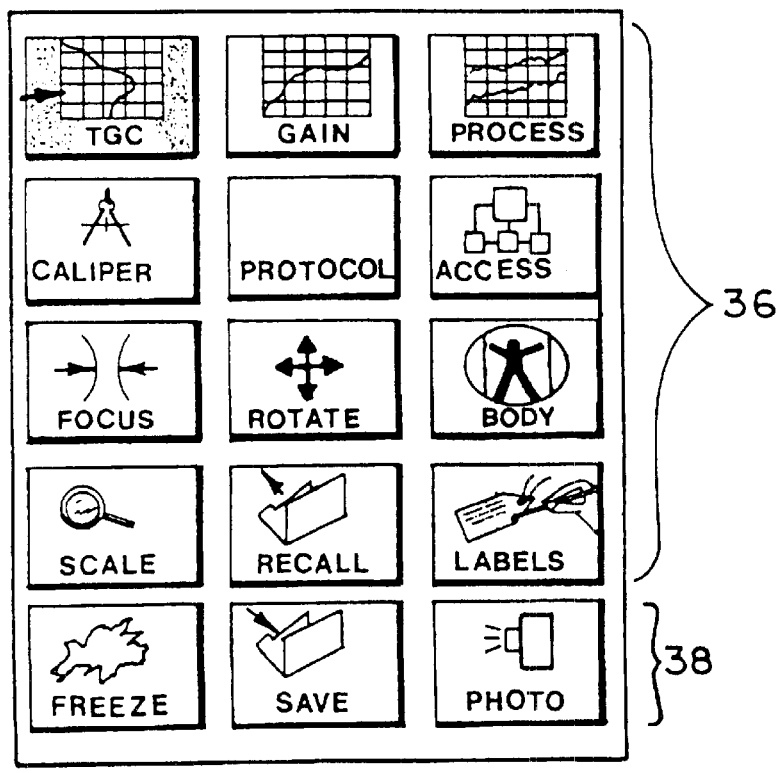
FIG. 2 diagrammatically illustrates another embodiment of the dynamic menu portion of the virtual control user interface.

FIG. 2 diagrammatically illustrates a dynamic menu region 36 and display screen area 38 which shows an icon for the various commands or functions as well as the English language equivalent or abbreviations for those functions. In general, there are two different display embodiments discussed herein. These different embodiments are meant to reveal the flexibility of the virtual control user interface and not to limit the claims appended hereto. The icon shown in FIG. 2 show TGC as a vertically oriented curve since the TGC actually changes the sweep of the echo response generated by the ultrasound scan head, a gain icon which is a horizontally oriented curve, a process icon as two synchronized wave forms; a caliper or measurement icon revealed by an illustration of a caliper; protocol (which may be represented by a book or a note pad indicating which medical protocol should be selected for a particular ultrasonic scan), an access icon which reveals a central box with peripheral units connected from the central box (representing the ultrasound processor which is electronically connected to certain access items such as VCR's, CD ROM writers and readers, Laps and modems linked to enhanced computerized data bases), a focus control icon, a rotate image icon comprising of four arrows outwardly directed from a central square; a body marker icon shown as a body; a scale or zoom icon illustrated by a magnifying glass; a recall image or electronic file icon shown as a file folder with an arrow pointing outbound therefrom, a label or annotation icon illustrated by a hand holding a pen or a pencil which is writing on a note pad. In screen display area 38, icons representing a freeze image signal (shown as a snowflake), a save image icon shown as a file with an arrow pointed to the file and a photo icon shown as a camera.

The freeze function enables the user to take a freeze fame of the ultrasound image currently retained in the temporary memory of the ultrasound processor. As can be appreciated, the acquisition of ultrasonic signals occurs in real time and the ultrasound processor unit continuously receives new electronic signals from the ultrasound scan head. Once the operator identifies a particularly good image (represented by a multiplicity of electronic signals currently displayed on the display monitor), the operator can freeze frame that electronic image and further process that image as described hereinafter. The user functions of saving an electronic image as well as generating a photograph of the electronic image are fairly well known. Saving an electronic image enables the user to electronically store the ultrasound scan image into the ultrasound processor memory (discussed later in conjunction with FIG. 25) and further to save it into other electronically attached computer peripheral elements. The photo function is also readily apparent to users of pre-existing ultrasound processors. For example with respect to obstetrical ultrasonic techniques, physicians may want a printed image of the frozen or selected electronic image captured by the ultrasound processor. The user can select the photo function and a POLAROID type photograph is generated by the ultrasound processor or an appropriately configured peripheral equipment.

Figure 3A:
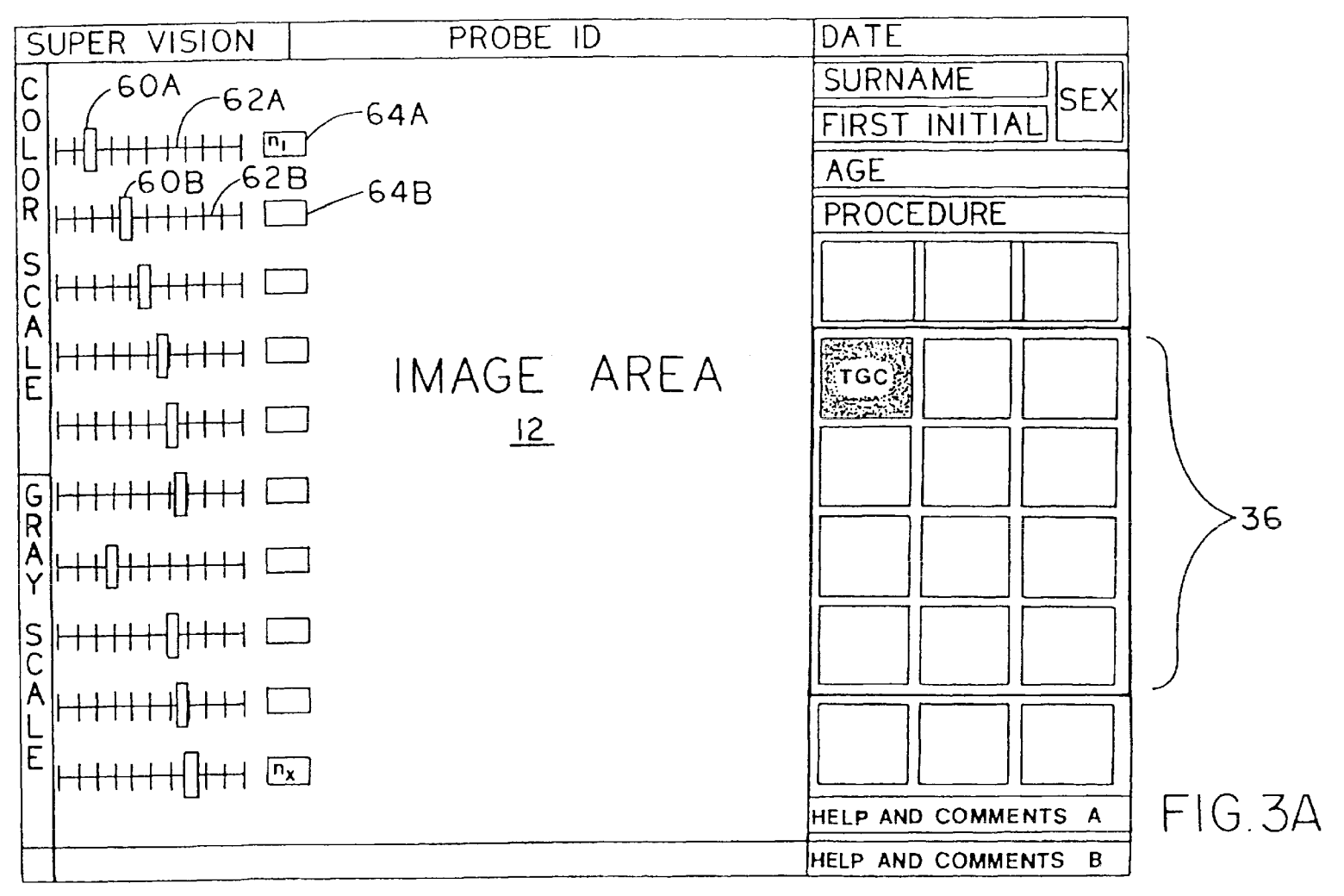
Figure 3B:
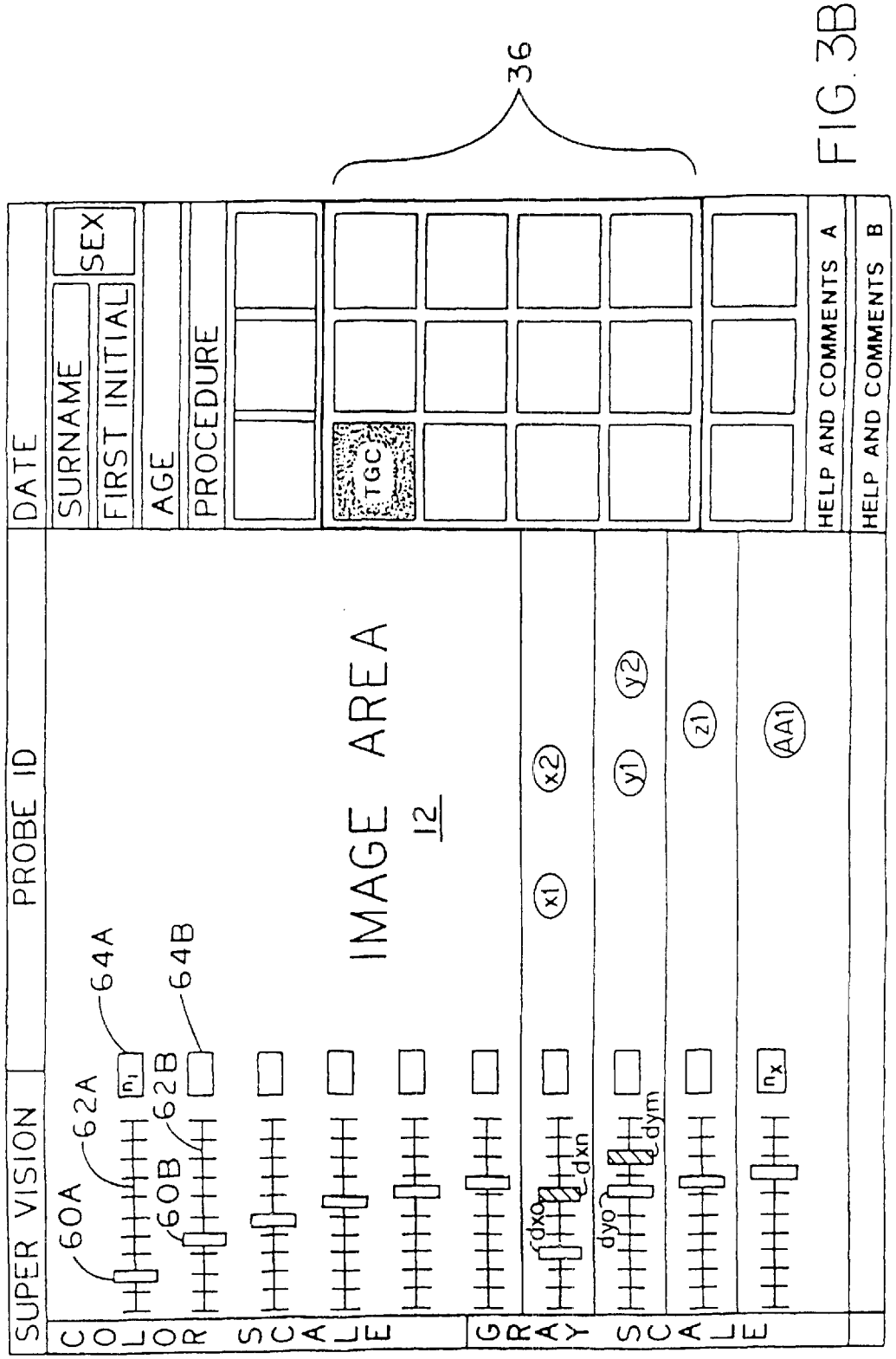
FIG. 3 diagrammatically illustrates the total gain control (TGC) user interface in one embodiment.

FIGS. 3 and 4A, 4B and 4C diagrammatically illustrate a secondary menu level associated with the TGC or time gain control virtual control user interface in accordance with the present invention. In FIG. 3, only the TGC functional element has been illustrated. Since the TGC or time gain control of the ultrasound processor affects generally the depths and echo responsiveness of the ultrasound scan head, users are generally accustomed to moving a plurality of slide switches or rotating a plurality of knobs to adjust the image and the depth of the image displayed in image area 12. In FIG. 3, the virtual control user interface is configured with a plurality of user actually slide or bar switches 60*a*, 60*b*, among others. To change the TGC at the upper level of scan image (for an illustration of the scan image, please refer to FIG. 14), the user would locate the cursor on the virtual image for slide bar 60*a*, click the mouse or actuate the push button the track ball, drag the virtual image of the slide bar 60 to another point on virtual image track 62*a* and then release the mouse switch or track ball switch. Alternatively, a touch type display screen is utilized, the operator could simply touch the virtual image of slide bar 60*a* and move the slide bar along virtual image line 62*a* to the appropriate position. Simultaneously with this change, the sonographic image in image area 12 is changed. Accordingly, the virtual control user interface in the present invention not only changes the ultrasonic image captured by the processor but also acts as a control mechanism to control the response of the ultrasonic scan head. Immediately adjacent each virtual image slide or control line 62*a*, 62*b*, is a display area showing the numerical value. Please refer to display 64*a* and 64*b*. To show the flexibility of the virtual control user interface, the user could save a particular screen setting or TGC screen setting using the save function. See menu bar area 38 in FIG. 2 or that same area in FIG. 1. Thereafter, the user could recall that TGC or gain setting for feature scans.

The flexibility of the present invention is also illustrated by reviewing the sequential figures of FIGS. 4A, 4B and 4C. In these figures, slide bar switches 60*a* and 60*b* are illustrated immediately adjacent the line representation of the signal generated by the ultrasound scan head. This is shown in graphic region 65. FIG. 4B illustrates that the cursor has been placed proximate virtual image of slide switch 60*g* and that slide switch has been changed to reduce the gain at that particular vertical location. Slide switched 60*g* and 60*h* have been changed and the height of curve 67 has been changed is noted by a comparison between FIGS. 4A and 4B.

The control user interface is shown in FIGS. 4A, 4B and 4C also include gain control slide switches 66 as well as smoothing function slide images 68. In comparing FIG. 4A and FIG. 4C, the smooth switch 68 has been changed and curve 67 is shown as distinctly linear as compared with the curves shown in FIGS. 4A and 4B. Of course, the actual virtual control user interface can be altered to include a larger number or a smaller number of slide switches then illustrated in FIG. 4 or FIG. 3. Also, when the sophistication of the ultrasound scan head improve, the user can simply replace the scan head interface unit (discussed in conjunction with FIG. 25), update the virtual control user interface software (illustrated in conjunction with FIGS. 1–24) without having to completely discard the ultrasound processor. Further, improvements in the control user interface can be easily adopted through the use of the software driven display modules illustrated herein. The software driven display module can be easily changed as compared with the hard-wired or hardware control configurations for other ultrasound processors.

Figure 5:
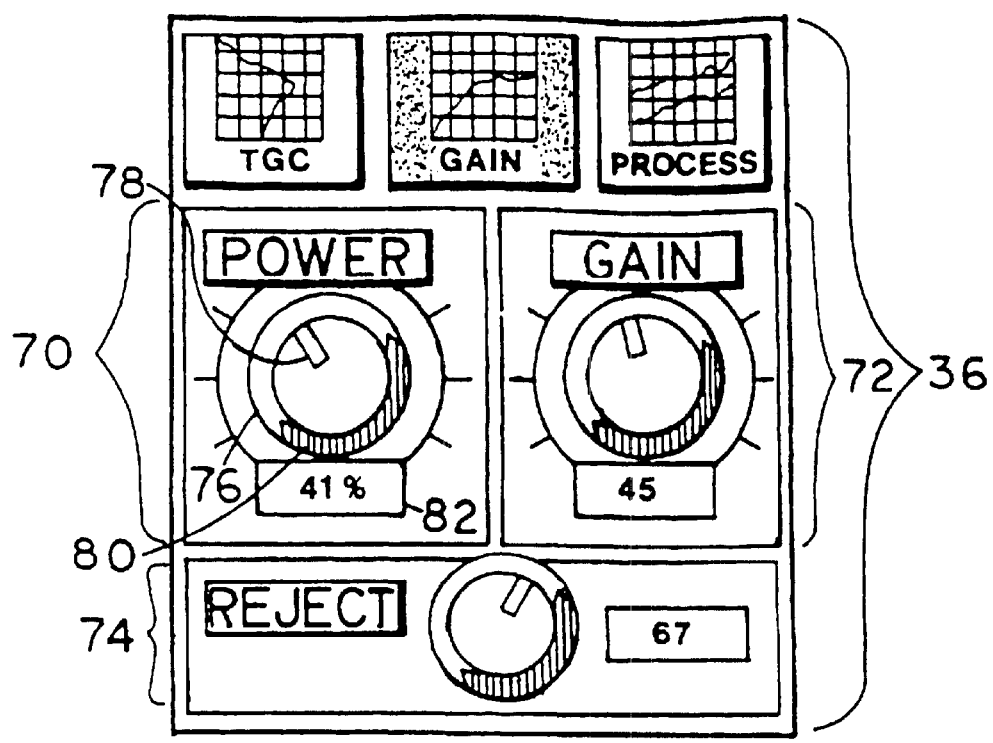
FIG. 5 diagrammatically illustrates the dynamic menu portion and sub-menu for the gain control interface.
Figure 6:
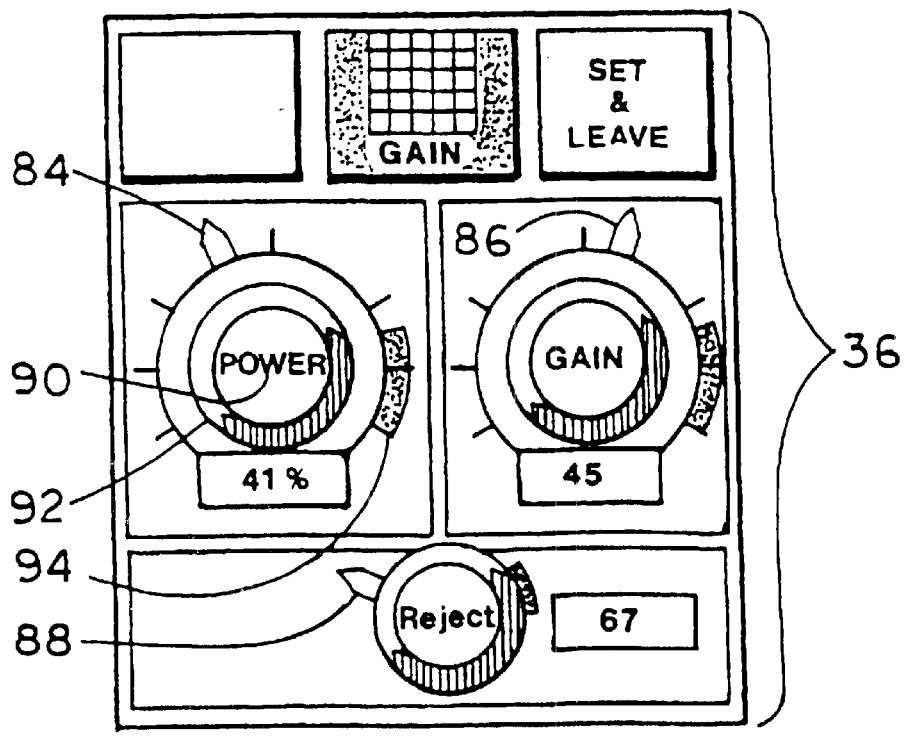
FIG. 6 diagrammatically illustrates another embodiment of the gain control secondary menu.

FIGS. 5 and 6 diagrammatically illustrate the secondary level associated with he gain function. FIG. 5 illustrates the use of virtual images of control knobs which he user may be accustomed to for a given hardware control configuration for another type of ultrasound processor. FIG. 5 illustrates that the user has activated the gain function from the main menu (see FIGS. 1 and 2) and the dynamic menu window 36 now reveals virtual images for the control knobs controlling the power (area 70) and he gain, area 72, and the reject signal control area 74. With respect to virtual image power area 70, a knob 76 is illustrated. Knob 76 has a virtual image line indicator 78 as well as red color danger areas 80. The red color danger areas are in a partial arcuate ring beginning at approximately 60% of total power level. The power level virtual display also includes a numerical display 82 which reveals to the operator of he actual power percentage level generated by the ultrasound scan head. The gain menu area 72 and the reject menu area 745 are similarly configured with virtual images of control knobs as well as those knobs indicating overload or danger areas indicated in red or other distinctive display colors in an arcuate band about the central rotative position.

If a touch type screen is utilized, the operator would touch the radial end of lineal position marker 78 (see power menu area 70) and moves his or her finger in a clockwise or counterclockwise manner about a pivot point generally in the center of the virtual control panel.

FIG. 6 diagrammatically illustrates another virtual control panel for the gain wherein the virtual knob controls include protruding virtual tabs 84, 86 and 88. If a touch type display screen is utilized, the operator would simply touch virtual knob 84, 86 and 88 and rotate his or her finger clockwise and counter clock wise about a central pivot position one of which is pivot position 90 for power knob 92. Also, FIG. 6 diagrammatically illustrates danger zones as shaded areas around the virtual knobs. One of these danger zones is shown as danger zone 94 around virtual knob 92, the virtual power control. FIG. 6 also illustrates a further functional aspect a "set and leave" command area that may be selected by the user. Once selected, the user can exit the sub-menu for the gain control. Another way the user can exit a particular sub-menu is to simply move the cursor beyond the dynamic window and actuate the control button on the mouse or the track ball.

Figure 7:
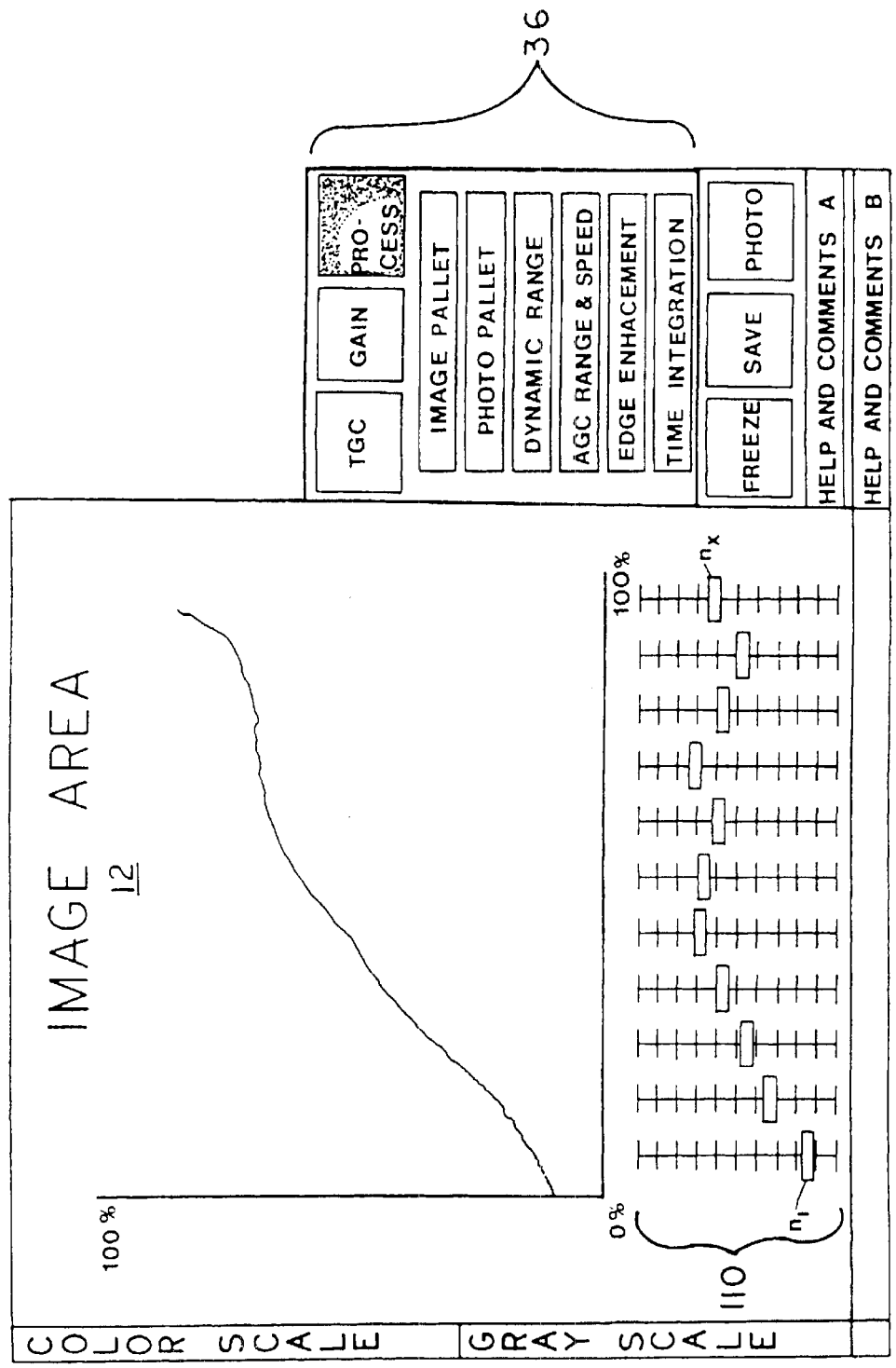
FIG. 7 diagrammatically illustrates a portion of the virtual control user interface sub-menu for the process or ultrasound image enhancement control interface.
Figure 9:
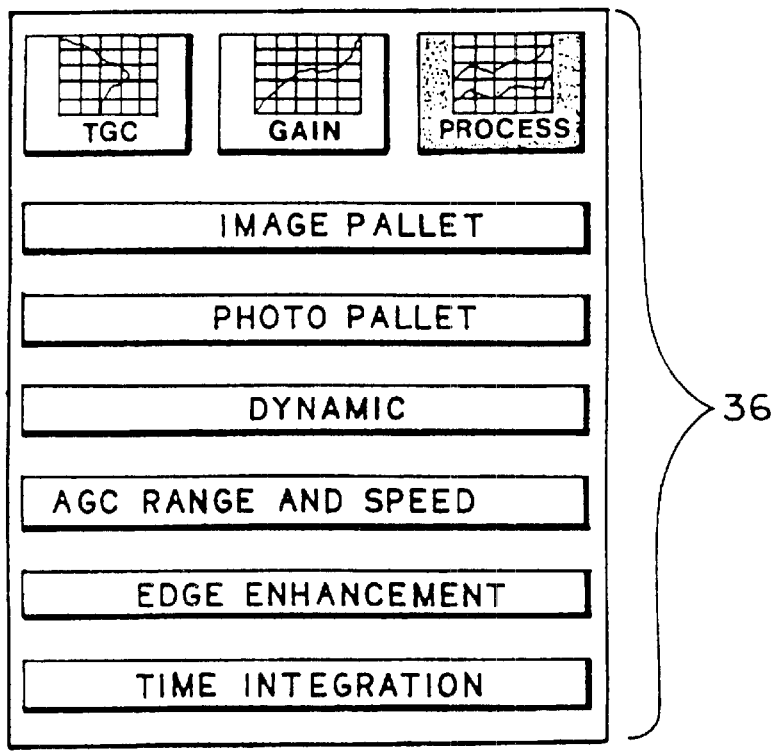
FIG. 9 diagrammatically illustrates a second embodiment of the dynamic menu window for the process sub-menu.

FIGS. 5, 7 and 9 illustrate various embodiments for the process sub-menus. One embodiment is shown in FIG. 7 wherein the dynamic display window 36 illuminates the process functions and shows various options available to the user to control the processing of the ultrasonic electronic signals obtained from the scan head. This processing includes changing the pallet on the image displayed in image area 12, changing the photographic pallet or color mix, changing the dynamic range for the scan signals, changing the automatic gain control (TGC) range and the speed or timing function for TGC enhancing the edge detection of the scan signal and providing time integration for the scan signal. As noted earlier, when the user moves the cursor over one of these areas, for example, image pallet as compared with dynamic range, that particular menu selection is highlighted or lights up. If the user wishes to activate that particular function, the user clocks the mouse button or tracking ball button or, in a touch screen situation, touches the screen to actuate the third menu level.

In the process menu, the image area is some what reduced and a pop up virtual control interface is displayed in lower region 110. As shown in FIG. 7, this virtual control interface consists of a number of slide switches $n_1$ through $n_x$ which can be actuated or moved by the user simply by placing the cursor on one of the virtual images of the slide bar and dragging the slide bar to the appropriate lineal position as indicated by the lines associated with each slide bar. As a further development, the actual power level or number could appear in the interior of the slide bar box. For example, $n_1$ could display 10% as being the image level for that particular range.

Figure 8:
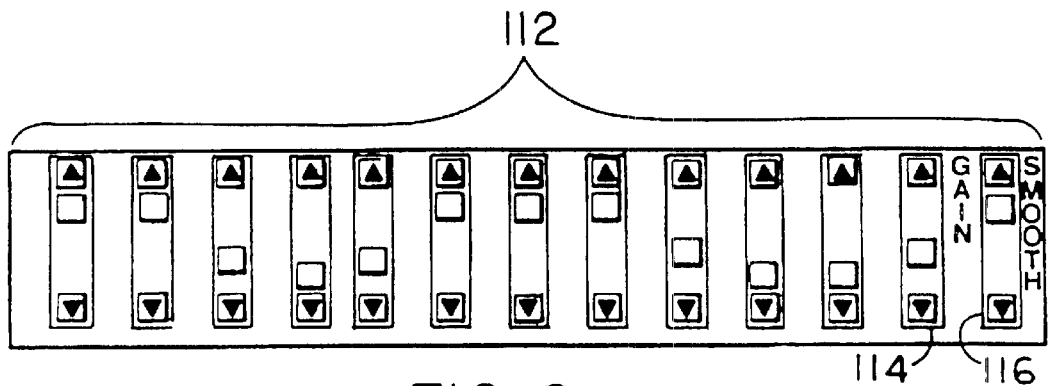
FIG. 8 diagrammatically illustrates a second embodiment for the image enhancement control user interface.

FIG. 8 diagrammatically illustrates another configuration for the video image process controls using a plurality of slide switches 112, two of which, shown as slide switches 114 and 116, which control the total gain of all the processing and scan signals as well as the smoothness characteristics between each amplification band. This feature is diagrammatically illustrated above in conjunction with FIGS. 4A–4C.

FIG. 9 diagrammatically illustrates dynamic menu window 36 showing the process sub-menu activated and indicates sub-level user control comparison images, image pallet, photo, pallet, dynamic range, TGC range and speed, edge enhancement and time integration.

Figure 10:
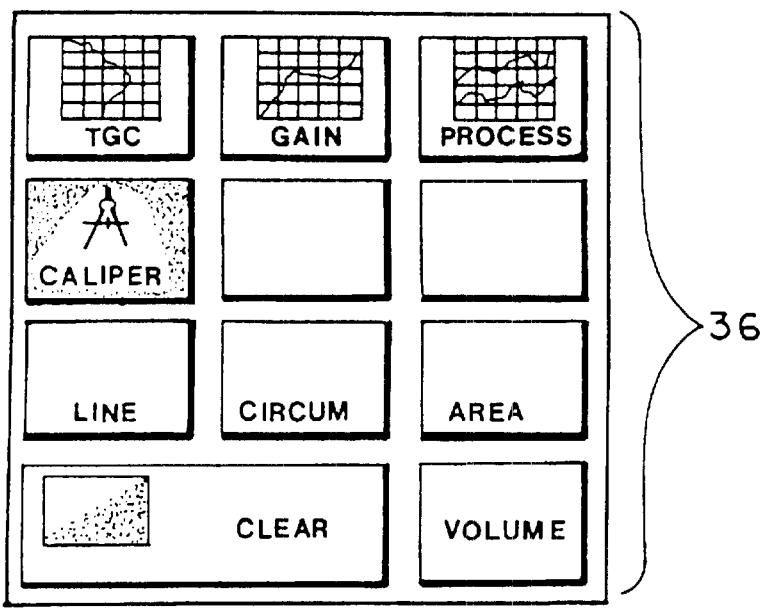
FIG. 10 diagrammatically illustrates one embodiment of the sub-menu display for the caliper or measurement user interface.
Figure 11:
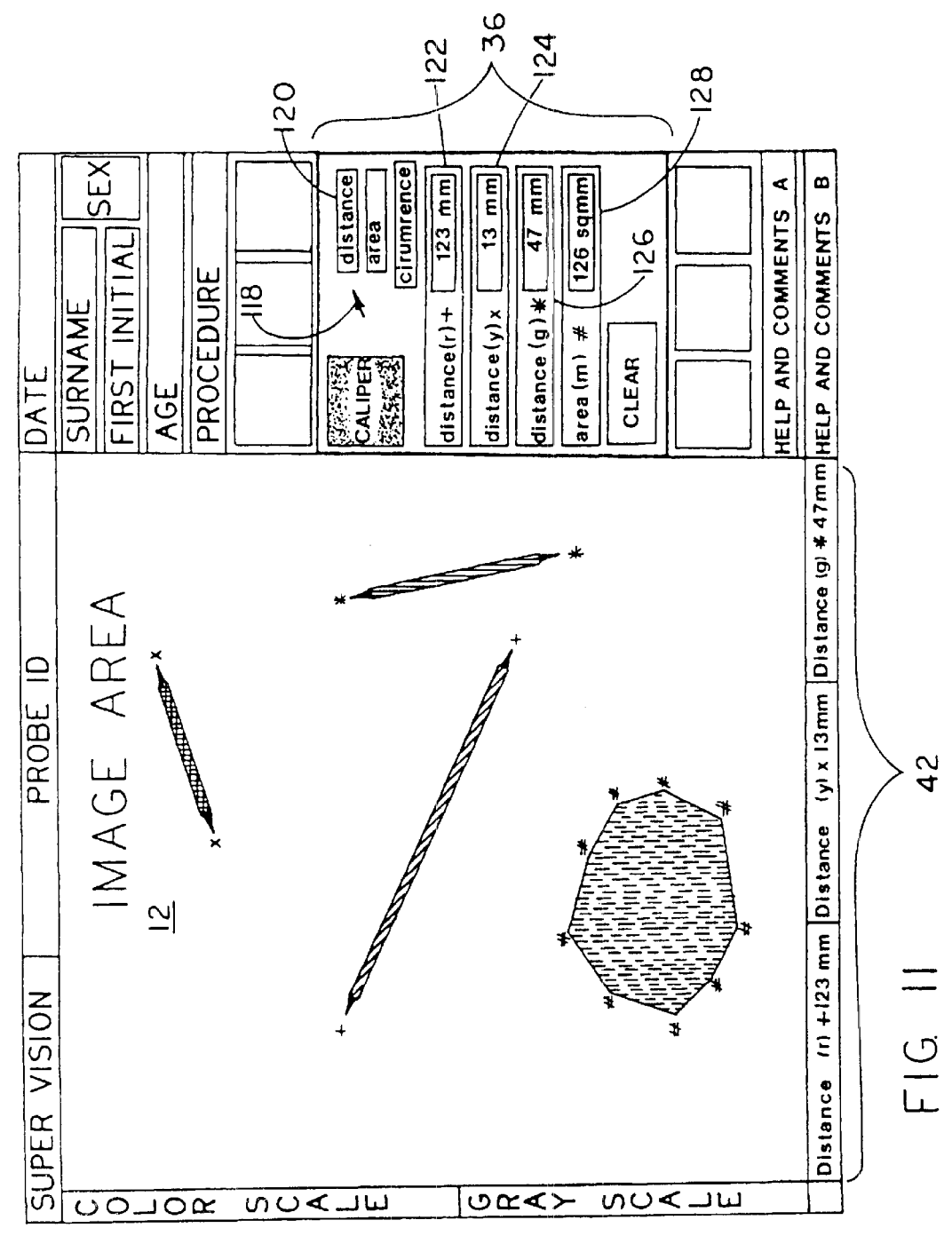

FIGS. 10 and 11 diagrammatically illustrate the caliper sub-menus which relate to measurement functions available to the user via the virtual control user interface. FIG. 10 shows that dynamic menu window 36 which includes an illuminated caliper button as well as reveals function buttons for measuring lines, measuring circumference, measuring area and measuring volume. Further, a function button enabling the user to clear a particular line is found in dynamic window menu 36. FIG. 11 shows a slightly different configuration with a cursor 118 proximately adjacent distance function button 120. Dynamic window 36 displays distance figures in region 122 (shown in red between the small plus signs in image area 12, the yellow distance shown between X's in image area 12, and a green distance G shown by asterisks in image area 12). The green line is illustrated in display region 126. In the screen area 128, an area is illustrated in magenta (M) in image area 12. In the lower menu region 42, the red distance, yellow distance and green line distance is shown in order to assist the user. The ability of the user to mark and measure the distance on a sonographic electronic image is important. For example, when using an ultrasound technique in conjunction with fetal development, the obstetrician seeks information regarding the length of certain fetal limbs as apparent in the ultrasonic electronic image. By enabling the user to easily control the processing of this ultrasound image (through TGC and gain virtual controls) and enabling the user to freeze that ultrasonic image on the screen (see for example FIG. 2, menu region 38 and the freeze control therein), the user can easily mark the image and actually make electronic drawings and immediate measurements for the physician and other health professionals interested in this information. The use of different colored lines and different display significantly enhances the operability and the user friendliness of the present system.

Figure 13:
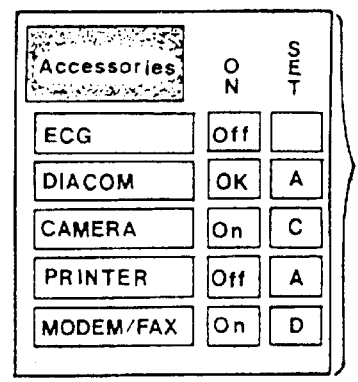
FIGS. 12 and 13 diagrammatically represent two embodiments for the dynamic window display for the accessories or access sub-menu level.
Figure 12:
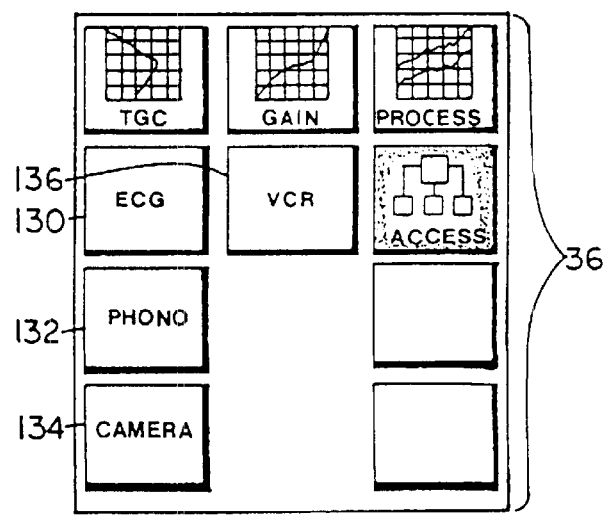

FIGS. 12 and 13 diagrammatically illustrate the access or accessory sub-menu for two embodiments. FIG. 12 shows menu buttons for electrocardiography information (ECG) virtual menu button 130, phono graphic or audio acquisition and access to other peripheral equipment on menu button 132, access to a camera peripheral equipment on virtual button 134 as well as access to a video tape recorder or VCR on menu button 136.

With respect to FIG. 13, other accessories are available such as a printer or a modem/facsimile machine. The preferred virtual control user interface incorporates a toggle on or toggle off type switch. However, as shown in FIG. 13, it may be appropriate to list the availability and on line accessibility of this equipment through various electronic computer ports.

With respect to FIG. 12, the photographic or audio linkage could be in the case of obstetrical use, the linkage of sounds obtained from a fetal monitor as well as the sonographic electronic file information. If this information from the audible fetal monitor as well as the electronic image from the sonogram taken of the pregnant mother is transferred to a specialist, the specialist at a very remote location could assess the condition of the mother by reviewing this information at his or her leisure. The ability to electronically obtain these signals, log these signals in and out of the system and store them in an electronic file as well as transfer this electronic file to others is an important feature of the present invention.

Figure 15:
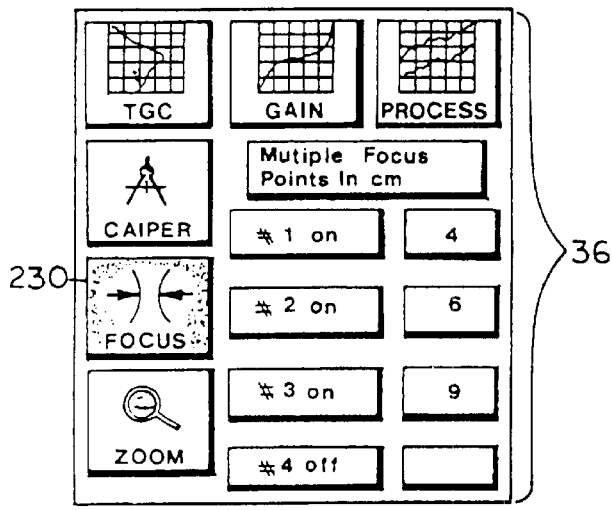
FIG. 15 diagrammatically illustrates the dynamic menu window for the focus control sub-menu utilized in conjunction with a second embodiment of the present invention.
Figure 14:
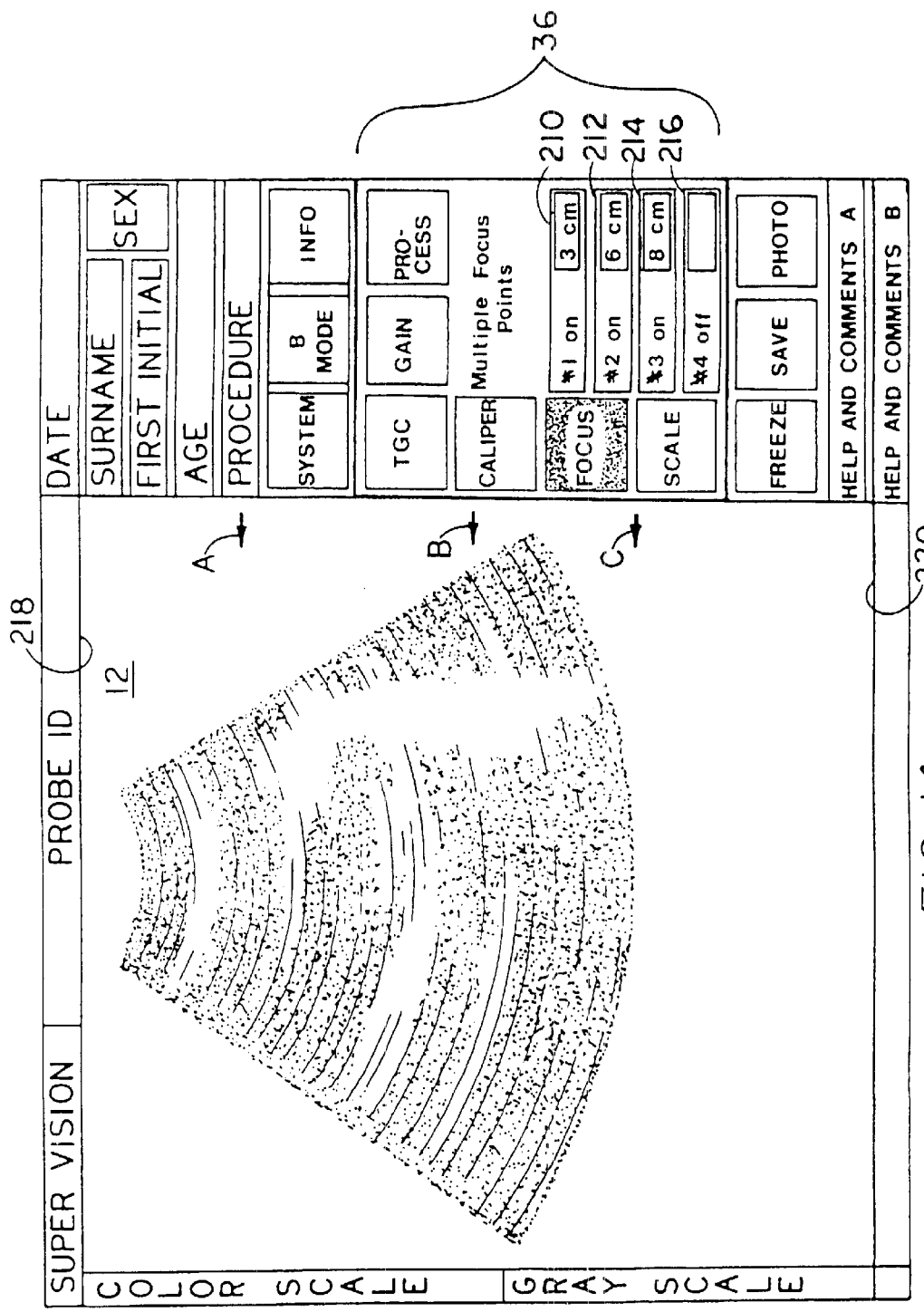
FIG. 14 diagrammatically illustrates the virtual control user interface for the focus control sub-menu and particularly one scanned image displayed in conjunction with the user interface.

FIGS. 14 and 15 diagrammatically illustrate the sub-menu levels for the focus control virtual function. in FIG. 14, an ultrasonic scan signal is illustrated. The focus virtual control button has been illuminated. Display areas 210, 212, 214 and 216 reveal the multiple focus points available to the operator. Particularly, focus points 1, 2 and 3 are on and the tissue depth is illustrated for each focal point. Focal point 4 is off. Arrows a, b and c correspond to focal points 1, 2 and 3 and, as displayed as such, the operator can change, for example, focal point 3, arrow c, by moving the cursor to arrow c and dragging arrow c to a point all the way to the top of the screen or at level 218 or all the way to the bottom of the screen at level 220. It should be noted that the illustrated ultrasound image is only exemplary in nature and may actually fill the entire image area 12. Also, it should be noted that the operator can drag any of the focal points beyond the other focal points already fixed.

FIG. 15 illustrates an alternative embodiment for the dynamic display window 23 region 36. Focus button 230 has been illuminated and the operator has turned on focal points 1, 2 and 3 but focal point 4 is off.

Figure 16:
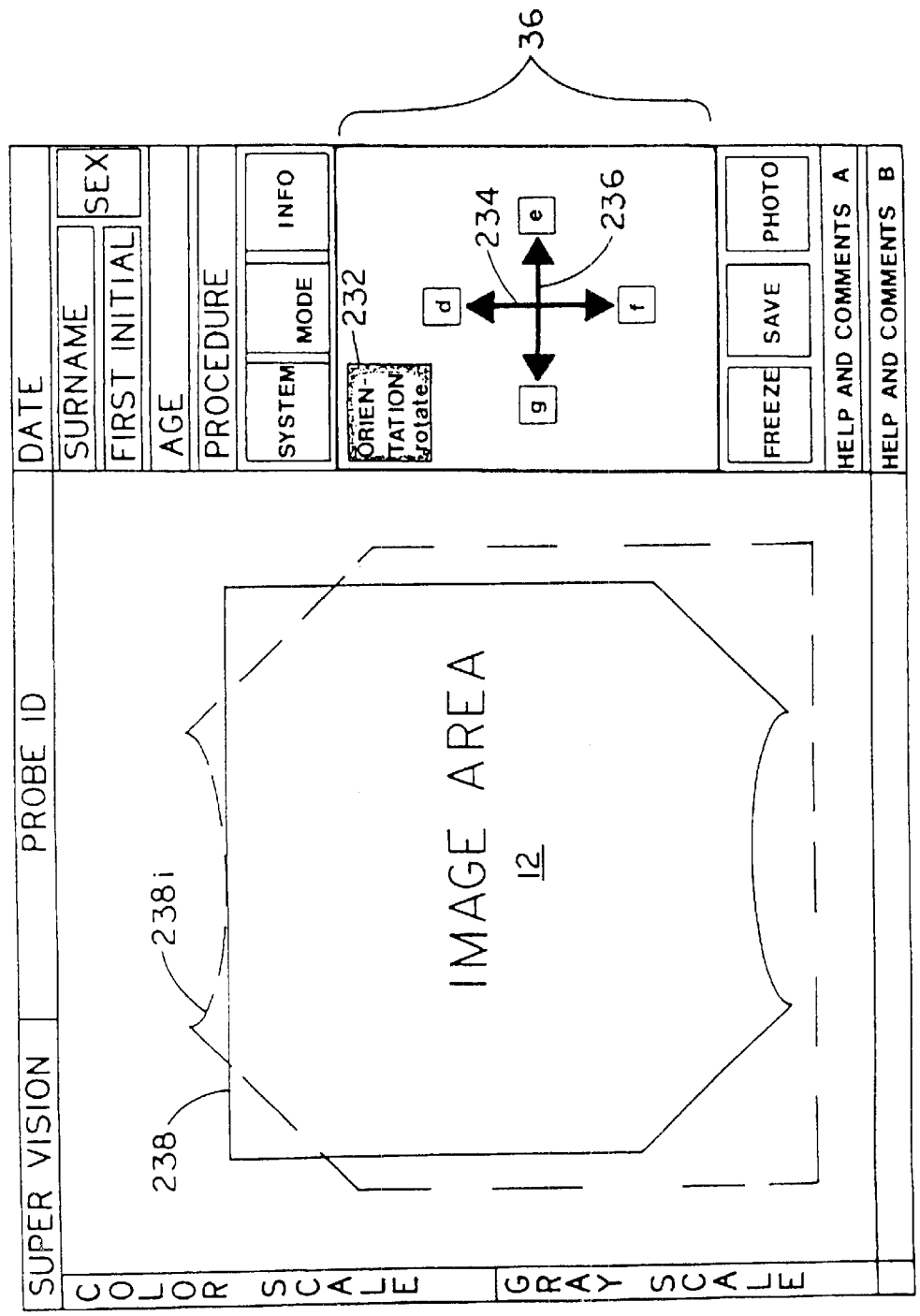
FIG. 16 diagrammatically illustrates the sub-menu level for the orientation or rotate image menu.

FIG. 16 diagrammatically illustrates the rotate image or orientation menu level such that rotate menu button 232 is illuminated. One virtual control interface could include the use of horizontal and vertical lines 234 and 236 each having an arrow head at opposing ends. Function buttons d, e, f and g may be placed at the terminal ends of those arrow heads. In a touch screen user interface, the user can simply touch display button d and move it up or down thereby moving the image 238 up or down or otherwise rotating the image clockwise or counter clockwise by simply rotating button d in the appropriate manner. Image 238 is rotated 180° as shown by image 238 in dashed lines in FIG. 16.

FIGS. 17, 18 and 19 diagrammatically illustrate the body marker or scan position virtual control user interface for the present invention. In FIG. 17, the body marker menu button 250 is illuminated and the operator can select from this sub-menu an image view 252, an icon placement function 254 and a probe placement function 256. As shown in FIG. 17, a rectilinear image block 260 has been placed on the left hip region of the female image. This indicates that the user has scanned that general region of the patient. FIG. 18 diagrammatically illustrates from the back views of a male as user marked icons 272 and 274. FIG. 19 is a further menu selecting enabling the user to select a particular scan icon such as by selecting rectilinear bar icon 276, Y bar icon 278 or arrow head icon 280. Function command 282 enables the user to rotate the particular scan icon along the body icon 290 or 292. In this illustrated embodiment, the body icons are provided with a plurality scan positions generally illustrated as a plurality of arrow heads 294 directed to the right side of the front of the female body. Of course, the virtual control user interface may have a plurality of arrow heads pointing and surrounding the body icons. In this embodiment, the user would select the appropriate position icon by selecting one of the position elements and also select the type of scan icon used at that body location. The scan icon represents a type of scan the user can draw on the patient. The program would then locate the selected scan icon at the selected body location. The user would also be able to rotate that scan icon to the appropriate position. This is shown with respect to body icon 292 wherein rectilinear scan icon 296 has been positioned at the lower back of body icon 292. The scan number has been displayed in display region 298. In the lower region 299, the operator is reminded of the current scan number which should be identified in conjunction with the ultrasonic scan acquired by the operator.

The body marker and various secondary and third menu levels may be particularly helpful when used in conjunction with protocol function. In other words, the user may select a particular protocol from the protocol function menus and then call up the body marker in order to assist the user to properly scan the correct area on the patient. Simultaneous with this canning and acquisition and signal processing by the user, the virtual control user interface could prompt the user to scan certain positions on the patient. This prompting could be incorporated as part of the body marker menu function.

The following protocol table illustrates the potential of the protocol menu function button (see FIG. 2). In the Protocol Menu Table which follows, the basic protocol for determining a certain kidney condition includes pelvocaliceal scans in multiple positions.

| | Protocol Menu Table | |
|---|---|---|
| A. | Basic Protocol | |
| | Outline Kidney | — |
| | Pelvocaliceal Scan Echo | |
| | Position 1 | — |
| | (move 5 cm) | |
| | Position 2 | — |
| | (move 5 cm) | |
| | Position 3 | — |
| B. | Supplemental (Baker Protocol | |
| C. | Dr. Kelly's Protocol | |

The protocol menu function could be coupled with the body markers in order to require the user to scan a minimum of three positions in order to fulfill the basic protocol. Upon storing and filing the three scans (using the save menu function button (FIG. 2)), the user would check off each element in the basic protocol. As stated in the protocol menu table, the user would be required to outline the kidney, and scan the internal body organ in three positions as specifically stated in the protocol.

If the physician ordering the sonogram wanted to use a different or a higher level protocol, the physician or other medical technician could load in this other protocol (the Baker protocol) and the Baker protocol could be listed for the user. Further, in come instances different doctors in the same medical office may want scans at different levels or at different frequencies. The protocol menu function button could provide this.

Figure 20:
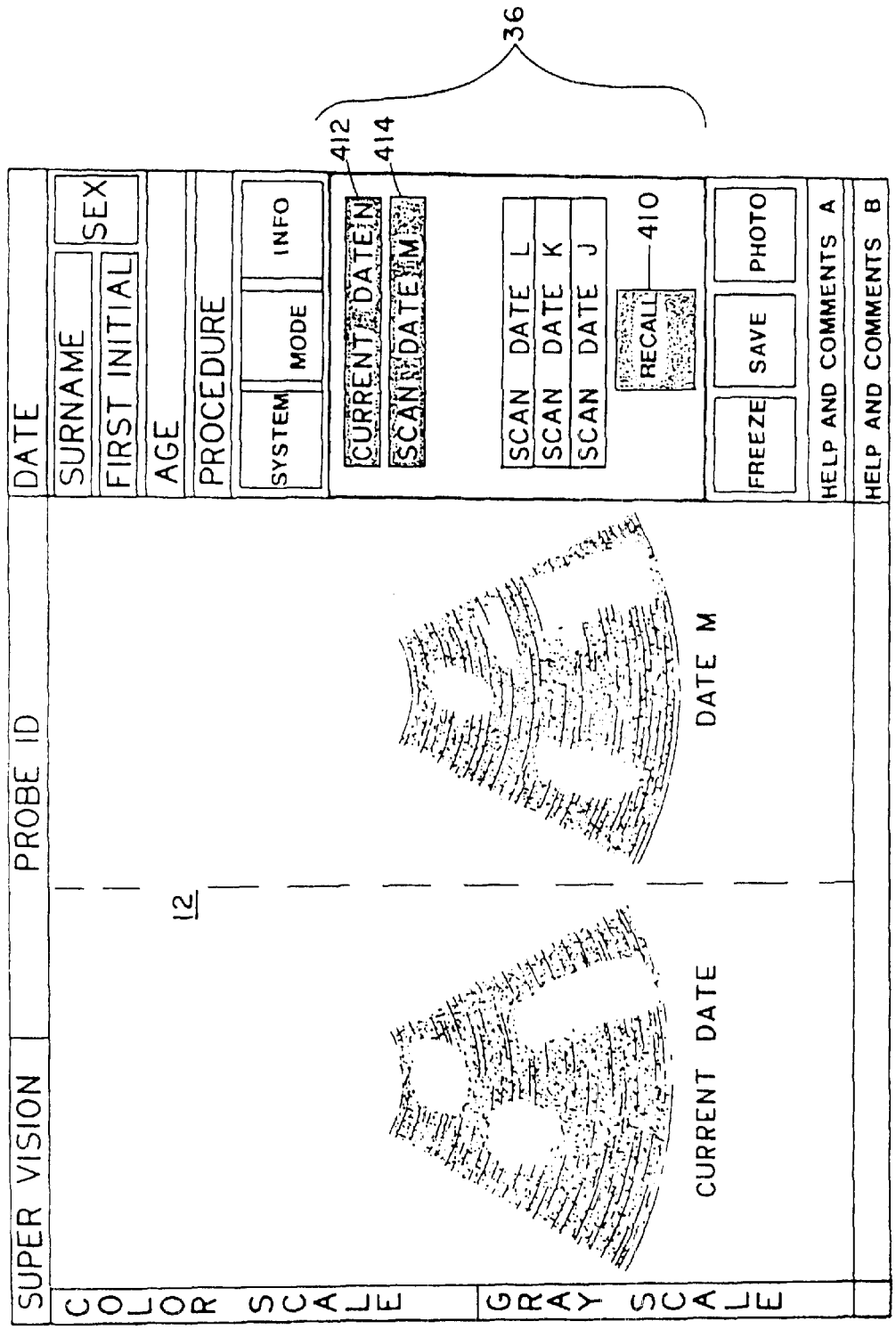
FIG. 20 diagrammatically illustrates the virtual control user interface showing a pair of ultrasound scanned images, one from an earlier scan and one from the current scan wherein these dual scan images are part of the recall sub-menu.

FIG. 20 diagrammatically illustrates the recall virtual control user interface. In the recall function, menu button 410 is illuminated and image display area 12 is divided into two sections, the first section showing a current scan (identified with the current date) and an earlier scan image identified by showing scan date M. In the illustrated instance, the user has selected menu button 412 showing the current date N and the earlier scan image of scan date M at function 414. The user has the ability to call up other scans, particularly those acquired at date L, date K and date J. With this feature, the user could configure electronic files showing the progression or regression of a certain disease.

Figure 21:
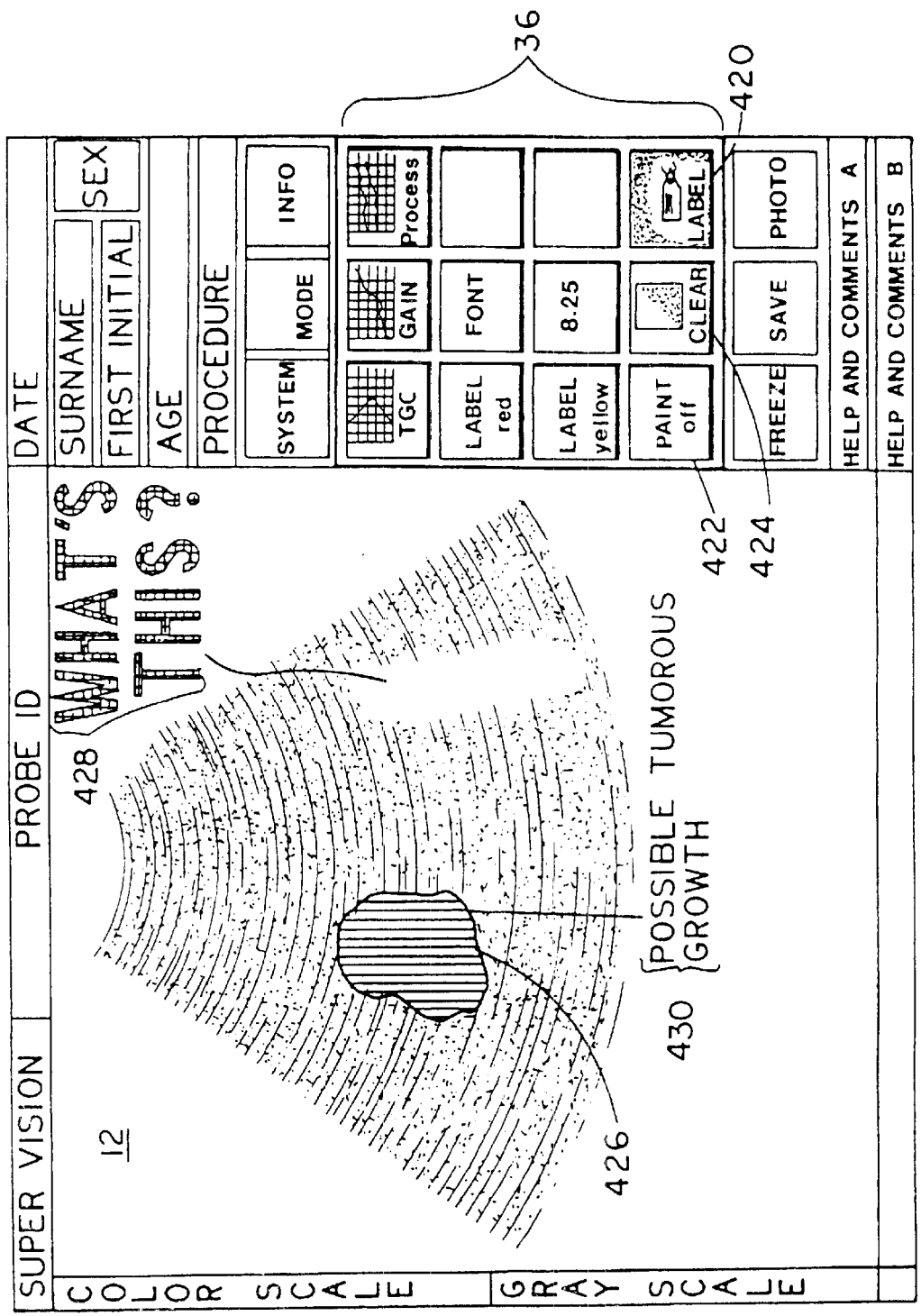
FIG. 21 diagrammatically illustrates the annotation feature of the control user interface.

FIG. 21 diagrammatically illustrates the sub-menu level for the annotate or label menu function. In this instance, the label or annotate menu button 420 is illuminated and dynamic menu display area 36 shows functional buttons for applying red labels, yellow labels, selecting the size of the print which is commonly known as font size, as well as a paint ON or paint OFF function button 422 and a clear function button 424. In the display image area 12, the physician has circled a region 426, for example, a red color and has typed the term "possible tumors growth" in order to highlight this region for other health care professionals. In contract to this red annotation on the electronic scan image is a yellow annotation "what's this" and a line leading to a certain electronic image region on the ultrasound scan. This different color annotation is identified in FIG. 21 with a double line. Also, the font size has been increased in text region 428 as compared with text region 430.

The annotations may be electronically stored in a separate file or maybe electronically stored in conjunction with the scanned image. If stored with the scan image, it may be necessary to enable the user to remove the annotations prior to viewing. For example, with respect to the recall function shown in FIG. 20, it may be preferable to remove the annotations from the recall image scan and to view the image scan side by side without any annotations. Also, it might be important to include in FIG. 20 the ability to recall in the annotations in the previous scan with a toggle on or toggle off menu button.

Figure 22:
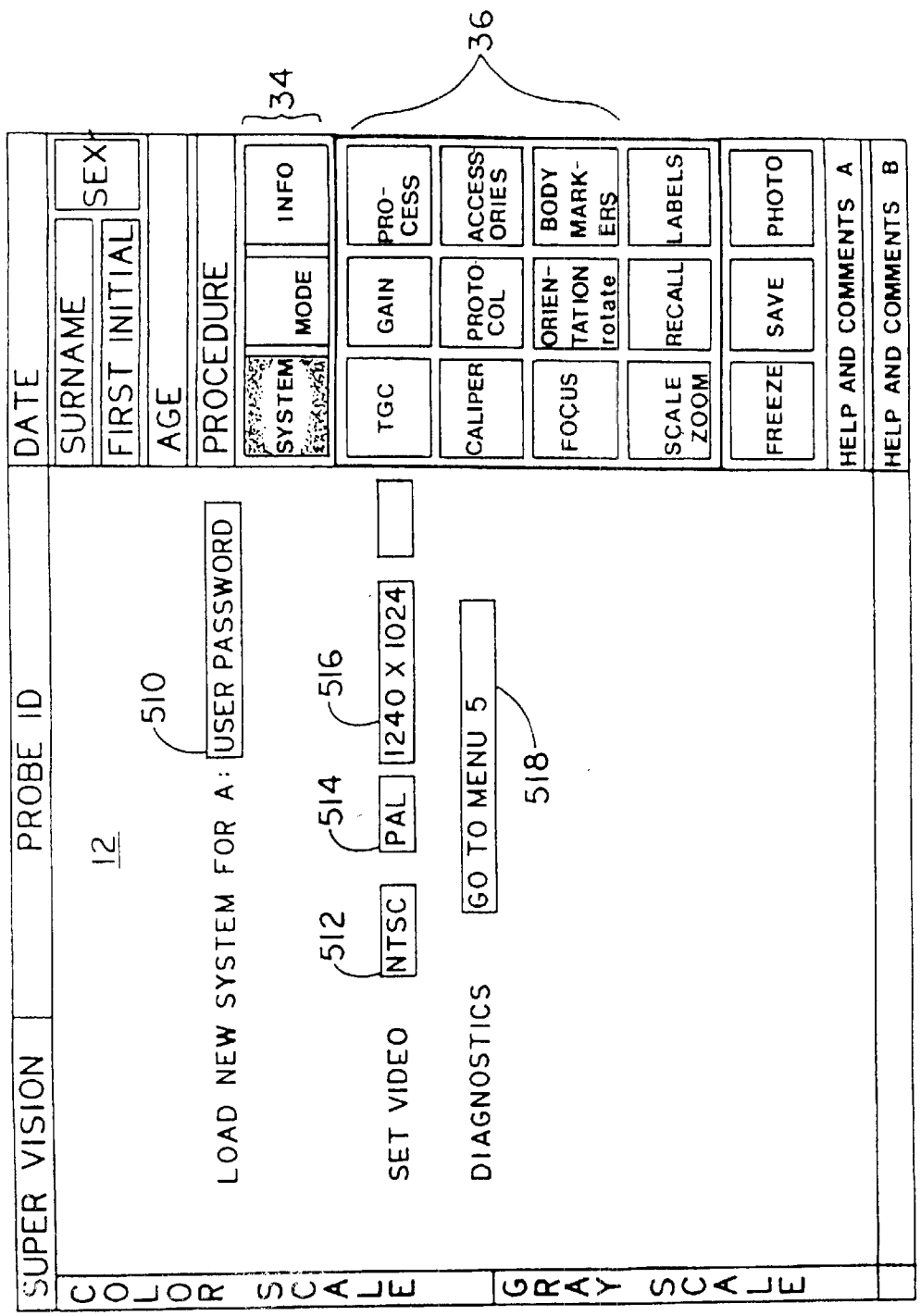
FIGS. 22, 23 and 24 diagrammatically illustrate the system sub-menu, mode sub-menu and information sub-menu used in conjunction with one embodiment of the present invention; and, FIG. 25 diagrammatically illustrates a system diagram for the ultrasound processor incorporating the virtual control user interface as well as that processor being electronically connected to various other computer elements. This figure also illustrates the inter-connectivity of the ultrasound processor with these other computer peripheral elements.
Figure 23:
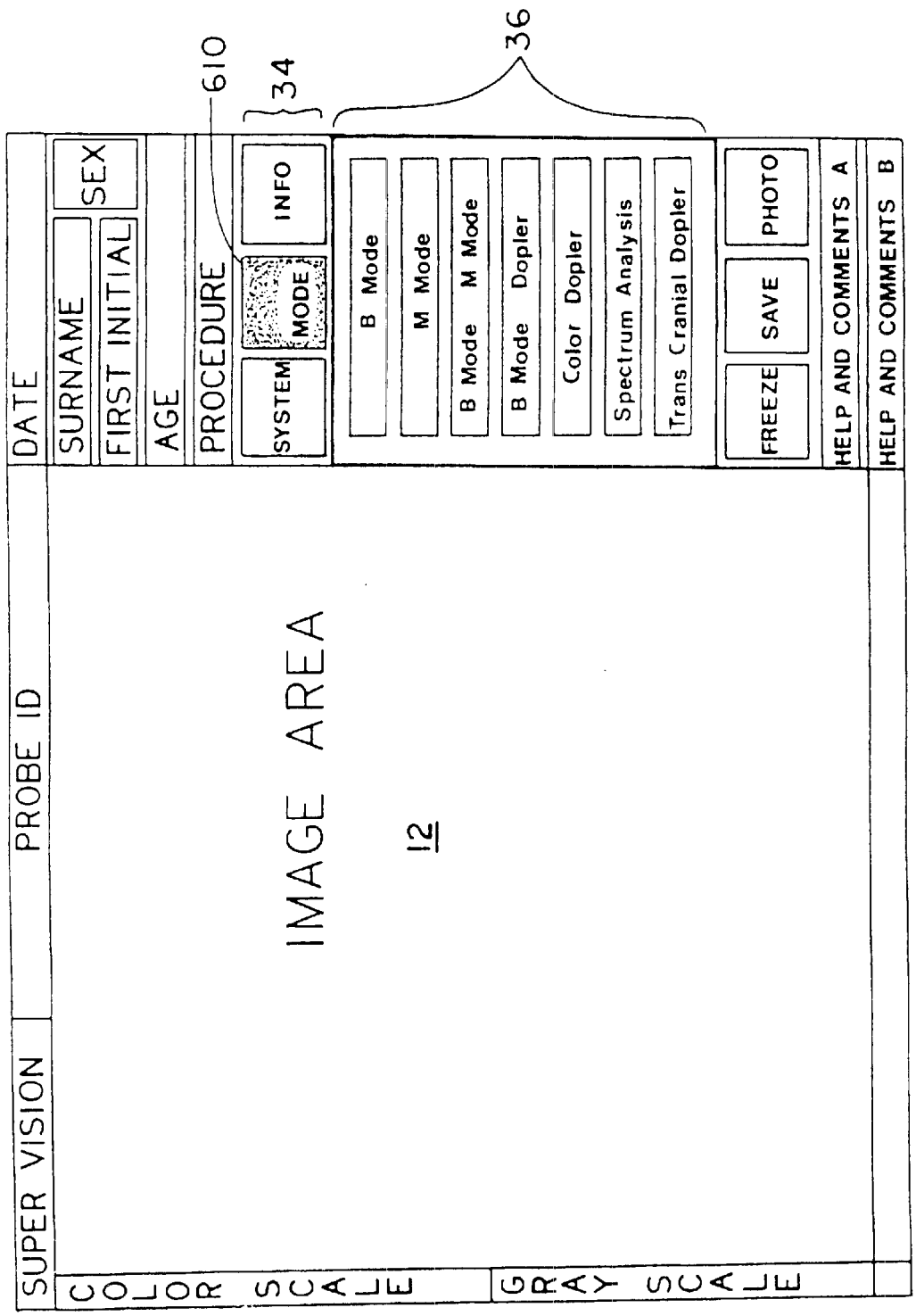

FIGS. 22, 23 and 24 diagrammatically illustrate certain overall features systems associated with menu bar 34 from the main menu. In FIG. 22 the system menu has been illuminated and the user is required to input his or her password or user Id in space 510, is required to set the video connection to NTC or PAL in section 512 and 514 and also to establish the size of the screen in display box 516. In order to enhance the user interface, the virtual control user interface may provide menu selections for the operator to select one of a plurality of selections to set up the system conditions. Menu box 518 enables the user to diagnosis and test the ultrasound processor as well as the ultrasound scan head and scan head interface unit.

In FIG. 23, the mode function button 610 has been actuated and therefor illuminated. In dynamic menu area 36, the operator can select which mode the ultrasound scan head is operating in, that is, b-mode and m mode, b mode and DOPPLER, color dOPPLER, spectrum analysis (involving a frequency analysis of the scan signal) or transcranial dOPPLER mode. Of course, the virtual control user interface can be modified in the event other ultrasound scan heads and general processing routines become available to the user.

In FIG. 24, the information or info menu button has been selected from menu bar 34. Further, menu bar 34 indicates that mail has been received by the ultrasound processor in spot 710. The information displayed in image area 12 provides general instructions for the user, for the renal transplant scan. This is somewhat similar to the protocol but really provides a mail box type environment where the user is instructed to use a certain type of ultrasound scan head and request certain scans such as length, width and depth as well as to send certain electronic files to physicians to their further input. Dynamic menu area 36 shows other available routine such as patient information, procedure information (currently displayed in image display area 12) protocol information, appointments, measurements, leave a message (for electronic mail) and supervision notes.

Returning to the main display menu in FIG. 1 and particularly the zoom or scale function button, the user, upon actuation of that function, can select the degree of magnification or complete enhancement of the scan image appearing in image area 12.

FIG. 25 diagrammatically illustrates the hardware for the ultrasound processor 810. In one embodiment, ultrasound processor 810 includes an internal bus 820 connecting a peripheral input/output card 822 with a modem card 724, a small computer system interface (SCSI) 826, a mother board 828, an ultrasound scan head interface card or unit 830 and a local area network input/output card 832. Mother board 828 includes random access memory or RAM 834 as well as a CPU or central processing unit chip 836. The CPU chip controls the handling of information and instructions on internal bus 820 the ultrasound scan head interface unit 830 is connected to an ultrasound scan head 840 as well as to a photograph production unit 842. The SCSI board 826 is connected to a CD read and write player 844. Modem 824 is connected via the telephone company 846 to a data base computer file 848. Computer peripheral input/output board 822 is connected to a local printer 850, a display monitor 852 (which may be a touch screen monitor) to a mouse 854 as well as to a keyboard 856. Keyboard 856 may additionally have a track ball 858 thereon.

The local area network input/output board 832 is connected to a file server 860 which in turn is connected to computer system $D_{r1}$ computer system $D_{r2}$ as well as telephone company 862 and a further computer system $D_{r3}$ file server 860 is also connected to remote printer 864.

An important aspect of the present invention is the ability to interconnect the ultrasound processor electronically to other computer data base files (data base files 848 via telephone company 846 and modem 824) as well as CD read-write units 844 in order to provide the user with the ability to quickly update any protocol and share the medical information provided by the accumulation of scanned data. In the event the physician or the medical office wishes to upgrade its ultrasound processor, the processor is simply disassembled and one of the cards is removed while another card is replaced. For example, the physicians may want to upgrade CPU 836 from a 486 machine to a PENTIUM or 586 type machine. This can be accomplished simply by removing mother board 828 and installing a faster mother board. Mother board 828 is further connected to a floppy drive 870, a hard drive 872, and a magnetic tape 874. Further, since the electronic images can be annotated and protocol established and made uniform throughout the entire medical office, the physician or other medical technician may share this electronic file with other physicians at computer systems $D_{r1}$, and $D_{r2}$ and even medical offices at very remote locations such as $D_{r3}$. In addition, the billing procedure for recapturing the cost for the ultrasound scans are easily enhanced. For example, the file server 860 can periodically pole ultrasound processor 810 in order to obtain information regarding the number of scans and the type of scans obtained on that processor. Further, with the integration of the present ultrasound processor system in the surgical arena, the current and earlier ultrasound electronic images could be delivered directly to the operating room such that the physician or surgeon conducting an operation can visually perceive the progression or regression of a particular disease or abnormality in a patient during the operation.

In one embodiment, the present virtual control user interface utilizes a 486 INTEL processor with approximately 1–2 mega bites of RAM.

The claims appended hereto are meant to cover modifications and changes within the spirit and scope of the present invention.

We claim:

1. A computer system electronically coupled to an ultrasound system comprising an ultrasound scan head and a scan head interface unit, said computer comprising:

a processor unit, a memory unit, a display monitor, a keyboard having a tactile user actuated control surface, an input/output interface for said display monitor and said keyboard, software in said memory unit for causing said processor unit to upload or download data from or to the ultrasound system; software for operating an ultrasound system with predetermined operating and display parameters including focus, time gain compensation, gain, display colors, frequency probe adjustments, doppler settings and shot sequences; and, a bus electronically coupling the ultrasound system to said processor unit, said memory unit, said display monitor, and said input/output interface for said display monitor and said keyboard;

said computer system including a virtual control user interface comprising:

software controls in said memory unit for manipulating, enhancing, annotating and post-processing images on said display monitor under the control of said processor unit and for storing said images, said images including live images of a hardware control configuration for a subject being viewed by the ultrasound system, or archived images of a hardware control configuration in said memory or retrieved from another ultrasound system or from an archival device;

said software controls including:

a plurality of computer driven gain control user interfaces, a plurality of computer driven ultrasound image enhancement control user interfaces, and at least one computer driven focus control user interface, said software controls having multiple menu levels for display of (a) said plurality of gain control images, (b) said plurality of ultrasound images and (c) said focus control images, and said software controls enabling the operating parameters of the ultrasound system and the display parameters of data from the ultrasound system to be altered by the user of said computer system to the predetermined operating and display parameters or to parameters desired by the user, said parameters including at least one of: focus, time gain compensation, gain, display colors, frequency probe adjustments, DOPPLER settings and shot sequences.

2. A computer system electronically coupled to an ultrasound system comprising an ultrasound scan head and a scan head interface unit, said computer comprising:

a processor unit, a memory unit, a display monitor, a keyboard having a tactile user actuated control surface, an input/output interface for said display monitor and said keyboard, software in said memory unit for causing said processor unit to upload or download data from or to the ultrasound system; software for operating an ultrasound system with predetermined operating and display parameters including focus, time gain compensation, gain, display colors, frequency probe adjustments, doppler settings and shot sequences; and, a bus electronically coupling the ultrasound system to said processor unit, said memory unit, said display monitor, and said input/output interface for said display monitor and said keyboard;

said computer system including a virtual control user interface comprising:

software controls in said memory unit for manipulating, enhancing, annotating and post-processing images on said display monitor under the control of said processor unit and for storing said images, said images including live images of a hardware control configuration for a subject being viewed by the ultrasound system, or archived images of a hardware control configuration in said memory or retrieved from another ultrasound system or from an archival device;

said software controls including:

a plurality of computer driven gain control user interfaces, a plurality of computer driven ultrasound image enhancement control user interfaces, and at least one computer driven focus control user interface, said software controls having multiple menu levels for display of (a) said plurality of gain control images, (b) said plurality of ultrasound images and (c) said focus control images;

said software controls enabling the operating parameters of the ultrasound system and the display parameters of data from the ultrasound system to be altered by the user of said computer system to the predetermined operating and display parameters or to parameters desired by the user, said parameters including at least one of: focus, time gain compensation, gain, display colors, frequency probe adjustments, DOPPLER settings and shot sequences; and a touch screen input converter responsive to a user's touch on said touch sensitive display monitor to convert the tactile input into a software command corresponding to the image proximally displayed on said touch sensitive display monitor.

* * * * *

UNITED STATES PATENT AND TRADEMARK OFFICE
CERTIFICATE OF CORRECTION

PATENT NO.    : 6,468,212 B1
DATED         : October 22, 2002
INVENTOR(S)   : Walter Guy Scott and Albert Vara It is certified that error appears in the above-identified patent and that said Letters Patent is hereby corrected as shown below:

<u>Title page,</u>
Item [75], Inventors, please change "Albert Vera" to -- Albert Vara --

Signed and Sealed this

Fifteenth Day of April, 2003

JAMES E. ROGAN
*Director of the United States Patent and Trademark Office*